US008895699B2

(12) United States Patent
Verdine et al.

(10) Patent No.: US 8,895,699 B2
(45) Date of Patent: Nov. 25, 2014

(54) STABILIZED COMPOUNDS HAVING SECONDARY STRUCTURE MOTIFS

(71) Applicant: President and Fellows of Harvard College, Cambridge, MA (US)

(72) Inventors: Gregory L. Verdine, Lexington, MA (US); Christian E. Schafmeister, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/680,905

(22) Filed: Nov. 19, 2012

(65) Prior Publication Data
US 2013/0211046 A1 Aug. 15, 2013

Related U.S. Application Data

(63) Continuation of application No. 12/796,212, filed on Jun. 8, 2010, now Pat. No. 8,324,428, which is a
(Continued)

(51) Int. Cl.
*C07K 1/113* (2006.01)
*C07K 1/00* (2006.01)
*C07K 1/04* (2006.01)
*C07K 14/00* (2006.01)
*C07K 14/47* (2006.01)

(52) U.S. Cl.
CPC . *C07K 1/00* (2013.01); *C07K 1/047* (2013.01); *C07K 1/113* (2013.01); *C07K 14/001* (2013.01); *C07K 14/4746* (2013.01)
USPC ........................................ 530/345

(58) Field of Classification Search
None
See application file for complete search history.

(56) References Cited

U.S. PATENT DOCUMENTS 4,730,006 A 3/1988 Bohme et al.
5,364,851 A 11/1994 Joran
(Continued)

FOREIGN PATENT DOCUMENTS

WO  WO-03/106491 A2  12/2003
WO  WO-2005/044839 A2  5/2005
WO  WO-2005/118634 A2  12/2005

OTHER PUBLICATIONS

Karle et al. Structural Characteristics of alpha-Helical Peptide Molecules Containing Aib Residues. Biochemistry. Jul. 24, 1990. vol. 29, No. 29, pp. 6747-6756.*
(Continued)

*Primary Examiner* — Jeffrey E Russel
(74) *Attorney, Agent, or Firm* — Wolf, Greenfield & Sacks, P.C.; C. Hunter Baker; Xiaohong Shou

(57) ABSTRACT

The present invention provides novel stabilized crosslinked compounds having secondary structure motifs, libraries of these novel compounds, and methods for the synthesis of these compounds libraries thereof. The synthesis of these novel stabilized compounds involves (1) synthesizing a peptide from a selected number of natural or non-natural amino acids, wherein the peptide comprises at least two moieties capable of undergoing reaction to promote carbon-carbon bond formation; and (2) contacting the peptide with a reagent to generate at least one crosslinker and to effect stabilization of a secondary structure motif. The present invention, in a preferred embodiment, provides stabilized p53 donor helical peptides. Additionally, the present invention provides methods for disrupting the p53/MDM2 binding interaction comprising (1) providing a crosslinked stabilized a-helical structure; and (2) contacting the crosslinked stabilized a-helical structure with MDM2.

18 Claims, 22 Drawing Sheets

Related U.S. Application Data continuation of application No. 11/148,976, filed on Jun. 9, 2005, now Pat. No. 7,786,072, which is a continuation of application No. 09/574,086, filed on May 18, 2000, now Pat. No. 7,192,713.

(60) Provisional application No. 60/167,634, filed on Nov. 26, 1999, provisional application No. 60/134,708, filed on May 18, 1999.

(56) References Cited

U.S. PATENT DOCUMENTS

| | | | |
|---|---|---|---|
| 5,446,128 | A | 8/1995 | Kahn |
| 5,708,136 | A | 1/1998 | Burrell et al. |
| 5,750,767 | A | 5/1998 | Carpino et al. |
| 5,811,515 | A | 9/1998 | Grubbs et al. |
| 5,824,483 | A | 10/1998 | Houston, Jr. et al. |
| 6,051,554 | A | 4/2000 | Hornik et al. |
| 6,610,657 | B1 | 8/2003 | Goueli |
| 7,083,983 | B2 | 8/2006 | Lane et al. |
| 7,192,713 | B1 * | 3/2007 | Verdine et al. ............ 435/7.1 |
| 7,786,072 | B2 * | 8/2010 | Verdine et al. ............ 514/21.4 |
| 8,324,428 | B2 * | 12/2012 | Verdine et al. ............ 562/553 |
| 2009/0326192 | A1 | 12/2009 | Nash et al. |
| 2011/0144303 | A1 | 6/2011 | Nash et al. |

OTHER PUBLICATIONS

Andrews, M.J. I. et al., "Forming Stable Helical Peptides Using Natural and Artificial Amino Acids," *Tetrahedron*, 55:11711-11743 (1999).

Armstrong, P. et al., "X=Y-ZH Systems as potential 1,3 dipoles. 5. Intramolecular cycloadditions of imines of α-amino acid esters.", *Tetrahedron*, 41(17):3547-3548 (1985).

Babine, R.E. et al., "Molecular Recognition of Protein-Ligand Complexes: Applications to Drug Design", *Chem. Rev.* 97:1359-1472 (1997).

Belokon, Y. N. et al., Improved Procedures for the Synthesis of (S)-2-[N-(N'-benzyl-prolyl) amino]benzophenone (BPB) and Ni9II) complexes of Schiff's bases derived from BPB and Amino Acids, *Tetrahedron: Asymmetry*, 9:4249-4252 (1998).

Belokon, Y. N. et al., "Chiral Complexes of Ni(II), Cu(I) as Reagents, Catalysts and Receptors for Asymmetric Synthesis and Chiral Recognition of Amino Acids", *Pure & Appl. Chem.*, 64(12):1917-1924 (1992).

Berendsen, H. J. C., "A glimpse of the Holy Grail?", *Science*, 282(5389):642-3 (Oct. 23, 1998).

Biagini, S. C. G. et al., "Cross-metathesis of Unsaturated α-amino Acid Derivatives", *J. Chem. Soc., Perkin Trans.*, 1:2485-2499 (1998).

Bierzynski, A. et al., "A Salt Bridge Stabilizes the Helix Formed by Isolated C-Peptide of RNase A", *Proc. Natl. Acad. Sci. USA*, 79:2470-2474 (1982).

Blackwell, H. E. et al., "Highly Efficient Synthesis of Covalently Cross-Linked Peptide Helices by Ring-Closing Metathesis", *Angew. Chem. Int. Ed.*, 37(23):3281-3284 (1998).

Bracken, C. et al., "Synthesis and Nuclear Magnetic Resonance Structure Determination of an α-Helical, Bicyclic, Lactam-Bridged Hexapeptide", *J. Am. Chem. Soc.*, 116:6431-6432 (1994).

Bradley, C. M. et al., "Limits of Cooperativity in a Structurally Modular Protein: Response of the Notch Ankyrin Domain to Analogous Alanine Substitutions in Each Repeat", *J. Mol. Biol.*, 324(2):373-86 (Nov. 22, 2002).

Burger, K. et al., "Synthesis of a-(trifluoromethyl)-substituted a-amino acids. Part 7. An efficient synthesis for a-trifluoromethyl-substituted w-carboxy a-amino acids.", *Chemiker-Zeitung*, 114(3):101-104 (1990).

Clark, T. D. et al.,"Supramolecular Design by Covalent Capture. Design of a Peptide Cylinder via Hydrogen-Bond-Promoted Intermolecular Olefin Metathesis", *J. Am. Chem. Soc.*, 117:12364-12365 (1995).

Cusack, N. J. et al., "2,4,6-Tri-Isopropylbenzenesulphonyl Hydrazide: A Convenient Source of Di-Imide", *Tetrahedron*, 32:2157-2162 (1976).

Formaggio, F. et al., "Inversion of 310-Helix Screw Sense in a (D-aMe)Leu Homo-tetrapeptide Induced by a Guest D-(aMe)Val Residue", *Journal of Peptide Science*, 1:396-402 (Wiley & Sons, Ltd., Italy, 1995).

Furstner, A. et al.,"Nozaki-Hiyama-Kishi Reactions Catalytic in Chromium", *J. Am. Chem. Soc.*, 118:12349-12357 (1996).

Gante, J., "Peptidomimetics—Tailored Enzyme Inhibitors", *Angew. Chem. Int. Ed. Engl.*, 33:1699-1720 (1994).

Giannis, A. et al., "Peptidomimetics for Receptor Ligands-Discovery, Development, and Medical Perspectives",*Angew. Chem. Int. Ed. Engl.*, 32:1244-1267 (1993).

Goodson, L. H. et al., "Potential Growth Antagonists. I. Hydantoins and Disubstituted Glycines", *Journal of Organic Chemistry*, 25:1920-1924 (1960).

Greenfield, N. et al., "Computed Circular Dichroism Spectra for the Evaluation of Protein Conformation", *Biochemistry*, 8(10):4108-4116 (1969).

Greenlee, W. J. et al., "A general synthesis of alpha-vinyl-alpha-amino acids", *Tetrahedron Letters*, 42:3999-4002 (1978).

Grubbs, R. H. et al., "Ring-Closing Metathesis and Related Processes in Organic Synthesis", *Acc. Chem. Res.*, 28:446-452 (1995).

Guinn, R. M. et al., "Synthesis and Characterization of Polyamides Containing Unnatural Amino Acids", *Biopolymers*, 35(5):503-512 (John Wiley & Sons, Inc., USA, 1995).

Jackson, D. Y. et al., "General Approach to the Synthesis of Short α-Helical Peptides", *J. Am. Chem. Soc.*, 113:9391-9392 (1991).

Karwoski, G. et al., "Lysinonorleucine Cross-Link Formation in Alpha Amino Heptenoic Acid-Substituted Peptide Derivatives", *Biopolymers*, 17:1119-1127 (John Wiley & Sons, Inc., USA, 1978).

Kaul, R. et al., "Stereochemical Control of Peptide Folding", *Bioorganic & Medicinal Chemistry*, 7:105-117 (1999).

Kazmaier, U., "Synthesis of Quaternary Amino Acids Containing β,γ- as well as γ,δ-Unsaturated Side Chains via Chelate-Enolate Claisen Rearrangement", *Tetrahedron Letters*, 37(30):5351-5354 (Elsevier Science Ltd., Great Britain, 1996).

Kotha, S. et al., "Modification of Constrained Peptides by Ring-Closing Metathesis Reaction", *Bioorg. Med. Chem. Lett.*, 11:1421-1423 (2001).

Kussie, P. H. et al., "Structure of the MDM2 Oncoprotein Bound to the p53 Tumor Suppressor Transactivation Domain", *Science*, 274:948-953 (1996).

Lacombe, P. et al., "Reduction of Olefins on Solid Support Using Diimide", *Tetrahedron Letters*, 39:6785-6786 (1998).

Leduc, A.-M. et a/., "Helix-stabilized cyclic peptides as selective inhibitors of steroid receptor-coactivator interactions", *Proc. Natl. Acad. Sci, USA*, 100(20):11273-8 (Sep. 30, 2003).

Ngo, J. T. et al., "Computational complexity, protein structure prediction, and the levinthal paradox.", In *The Protein Folding Problem and Tertiary Structure Prediction*. K. Merc, Jr., et al. Eds., 491-495 (1994).

Phelan, J. C. et al., "A General Method for Constraining Short Peptides to an α-Helical Conformation", *J. Amer. Chem. Soc.*, 119(3):455-460 (1997).

Qiu, W. et al., "Convenient, Large-Scale Asymmetric Synthesis of Enantiomerically Pure trans—Cinnamylglycine and -α-Alanine", *Tetrahedron*, 56:2577-2582 (2000).

Rich, D. H. et al., "Synthesis of the ctostatis cyclic tetrapeptide, chlamydocin." *Tetrahedron Letters*, 24(48):5305-5308 (1983).

Rudinger, J., "Characteristics of the amino acids as components of a peptide hormone sequence.", In *Peptide Hormones*. J. A. Parsons, ed. University Park Press. Jun. 1976; pp. 1-7.

Sattler, M. et al., "Structure of Bcl-X$_L$-Bak Peptide Complex: Recognition Between Regulators of Apoptosis", *Science*, 275:983-986 (1997).

Schinzel, R. et al., "The phosphate recognition site of *Escherichia coli* maltodextrin phosphorylase.", *FEBS Lett.*, 286(1-2):125-8 (Jul. 29, 1991).

Scholtz, J. M. et al., "The Mechanism of α-Helix Formation by Peptides", *Annu. Rev. Biophys. Biomol. Struct.*, 21:95-118 (1992).

(56) References Cited

OTHER PUBLICATIONS

Tanaka, M., "Design and synthesis of non-proteinogenic amino acids and secondary structures of their peptides.", *Yakugaku Zasshi.*, 126(10):931-44 (Oct. 2006).

Voet, D. et al., Biochemistry, Second Edition. John Wiley & Sons, Inc. 1995; pp. 235-241.

Williams, R. M. et al., "Asymmetric Synthesis of Monosubstituted and α,α-Disubstituted α-Amino Acids via Diastereoselective Glycine Enolate Alkylations", *J. Am. Chem. Soc.*, 113:9276-9286 (1991).

Designing Custom Peptide. from SIGMA Genosys, pp. 1-2. Accessed Dec. 16, 2004.

Office Action from parent U.S. Appl. No. 12/796,212 dated Feb. 17, 2011.

Office Action from parent U.S. Appl. No. 12/796,212 dated Oct. 18, 2011.

Office Action from U.S. Appl. No. 12/420,816 dated Feb. 9, 2012.

* cited by examiner

STABILIZED COMPOUNDS HAVING SECONDARY STRUCTURE MOTIFS

RELATED APPLICATIONS

This application is a continuation of U.S. patent application Ser. No. 12/796,212, filed Jun. 8, 2010, which is a continuation of U.S. patent application Ser. No. 11/148,976, filed Jun. 9, 2005, now U.S. Pat. No. 7,786,072; which is a continuation of U.S. patent application Ser. No. 09/574,086, filed May 18, 2000, now U.S. Pat. No. 7,192,713; which claims the benefit of priority to U.S. Provisional Patent Application Ser. No. 60/167,634, filed Nov. 26, 1999; and U.S. Provisional Patent Application Ser. No. 60/134,708, filed May 18, 1999; the specifications of all of which are hereby incorporated by reference.

GOVERNMENT SUPPORT

This invention was made with support from the National Institutes of Health (Grant No. GM051330); the government has certain rights to the invention.

BACKGROUND OF THE INVENTION

The important biological roles that peptides play as hormones, enzyme inhibitors, substrates, neurotransmitters, and neuromediators has led to the widespread use of peptides in medicinal chemistry as therapeutic agents. Through binding to receptors or enzymes, peptides are able to influence cell-cell communication and control vital cell functions such as metabolism, immune defense and reproduction. Babine et al., Chem. Rev. 1997, 97, 1359). Unfortunately, the utility of peptides as drugs is severely limited by several factors, including their rapid degradation by peptidases under physiological conditions, their poor cell permeability, and their lack of binding specificity resulting from conformational flexibility.

In response to these unfavorable characteristics of peptide drugs, many research groups have developed strategies for the design and synthesis of chemical compounds, known as "peptidomimetics", in which sensitive peptide moieties are removed and replaced with more robust functionalities. In particular, researchers have sought to improve peptide stability and cell permeability by replacing the amide functionality with groups such as hydroxyethylene, (E)-alkenes, carba groups and phosphonamide groups (see, Gante, J. Angew. Chem. Int. Ed. Engl. 1994, 33, 1699-1720, and references cited therein).

Another approach that researchers have taken in the development of peptide drugs is the study of, initiation of, and retention of peptide secondary structures. These secondary structures, α-helices, β-sheets, turns, and loops, are essential conformational components for peptides and proteins because bioactive conformations are fixed to a high degree by such structural elements. Because of the biological importance of these secondary structures, the development of novel structures incorporating these secondary structures has been a subject of intense research (see, for example, R. M. J. Liskamp, Recl. Trav. Chim. Pays-Bas 1994, 113, 1; Giannis, T. Kolter, Angew. Chem. Int. Ed. Engl. 1993, 32, 1244; P. D. Bailey, Peptide Chemistry, Wiley, N.Y., 1990, p. 182). In particular, the formation of α-helices by peptides has been of interest because many biologically important protein interactions, such as p53/MDM2 and Bcl-X1/Bak, are mediated by one protein donating a helix into a cleft of its α-helix-accepting partner. Unfortunately, it has been very difficult to mimic the approximately 12 amino acids (i.e., three turns of an alpha helix) required to form a stabilized isolated helical peptide. As described in "Bioorganic Chemistry: Peptides and Proteins", Chapter 12, Peptide Mimetics, Nakanishi and Kahn, the entire contents of which are incorporated herein by reference, most of the effort in the design and synthesis of α-helix mimetics has centered around N-termination initiation motifs. Furthermore, studies have been undertaken to understand the mechanisms of α-helix formation by peptides, and thus studies of helix-stabilizing side chain interactions, and template-nucleated α-helix formation have been investigated (see, J. Martin Scholtz and Robert L. Baldwin, "The Mechanism of α-Helix Formation by Peptides, Ann. Rev. Biophys. Biomol. Struct. 1992, 21, 95, the entire contents of which are incorporated herein by reference) in an attempt to understand α-helix formation to aid in the future development of stabilized α-helix structures.

Clearly, it would be desirable to develop novel methods to generate stabilized α-helical structures, as well as other secondary structures, to enable the investigation of complex structure-function relationships in proteins and ultimately to enable the development of novel therapeutics incorporating specific stabilized secondary structure motifs.

SUMMARY OF THE INVENTION

The present invention provides novel compounds having stabilized secondary structure motifs, and methods for their preparation. In general, the synthesis of these stabilized secondary structures involves (1) synthesizing a peptide from a selected number of natural or non-natural amino acids, wherein said peptide comprises at least two reactive moieties capable of undergoing a carbon-carbon bond forming reaction; and (2) contacting said peptide with a reagent to generate at least one crosslinker and to effect stabilization of a specific secondary structure motif In one embodiment, the present invention provides novel alpha helix structures having stabilizing crosslinkers, libraries of these novel alpha helix structures, and methods for the synthesis of these alpha helices and libraries thereof In certain embodiments, olefin metathesis reactions are utilized to generate these novel α-helical structures comprising (1) synthesizing a peptide from a selected number of natural or non-natural amino acids, wherein said peptide comprises at least two vinyl amino acids capable of undergoing an olefin metathesis reaction or comprises at least one divinyl amino acid and at least two vinyl amino acids capable of undergoing olefin metathesis reactions; and (2) contacting said peptide with a metathesis catalyst to generate at least one crosslinker and to effect stabilization of an alpha helix structure. In one preferred embodiment, at least two vinyl amino acids are incorporated into the peptide synthesis to generate at least one crosslinker. In another preferred embodiment, at least two vinyl amino acids and at least one divinyl amino acid are incorporated to generate at least two crosslinkers originating from the same amino acid. Alternatively, any combination of divinyl amino acids and vinyl amino acids may be incorporated to generate desired crosslinked structures. It will also be appreciated that in certain embodiments, one or more of either of these crosslinker motifs can be incorporated into a desired stabilized α-helix structure.

In another embodiment, the method of the present invention is utilized to provide stabilized p53 donor helical peptides by incorporating vinyl amino acids into this structural motif and reacting said vinyl amino acids to generate stabilized α-helical structures. Additionally, the present invention provides methods for disrupting the p53/MDM2 binding interaction comprising (1) providing a crosslinker stabilized α-helical structure; and (2) contacting said stabilized α-helical structure with MDM2.

As will be appreciated by one of ordinary skill in the art, in one embodiment, the novel compounds having stabilized secondary structure motifs of the present invention can be synthesized one-at-at time, using traditional peptide synthetic techniques, to generate a particular structural motif. In preferred embodiments, however, the these novel stabilized secondary structures are synthesized using combinatorial synthetic techniques, in solution or on the solid support, to generate diverse libraries of novel stabilized compounds having desired secondary structure motifs. Whether using traditional synthetic techniques or combinatorial synthetic techniques, the method of the present invention provides for the generation of compounds having desired stabilized secondary structure motifs that can be based on existing structural motifs (p53) or that can represent novel unnatural peptide secondary structure motifs to explore heretofore unknown biological interactions.

DESCRIPTION OF CERTAIN PREFERRED EMBODIMENTS

Figure 1:
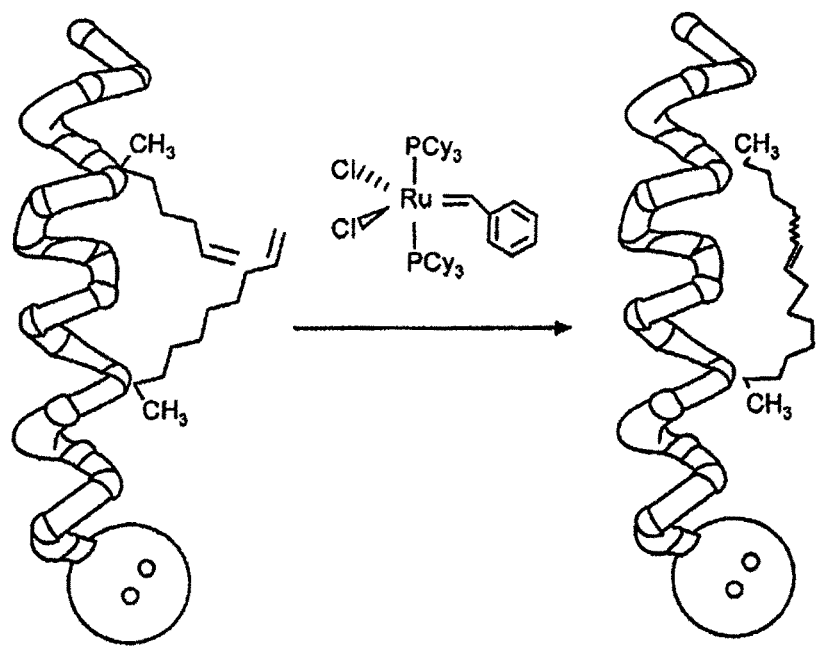
FIG. 1 depicts a particularly preferred embodiment of the invention in which a helix crosslinker is installed using olefin metathesis.

The present invention provides stabilized compounds having specific secondary structure motifs and improved methods for generating stabilized compounds having these specific secondary structure motifs. The novel stabilized compounds of the present invention are useful where such structural motifs are advantageous; for example, in drug design and delivery, and in but a few examples, as inhibitors of p53/MDM2 and Bak/Bcl-$x_L$ interactions.

In general, the synthesis of these stabilized secondary structures involves (1) synthesizing a peptide from a selected number of natural or non-natural amino acids, wherein said peptide comprises at least two reactive moieties capable of undergoing a C—C bond forming reaction; and (2) contacting said peptide with a reagent to generate at least one crosslinker and to effect stabilization of a specific secondary structure motif In one embodiment, the present invention provides novel alpha helix structures having stabilizing crosslinkers, libraries of these novel alpha helix structures, and methods for the synthesis of these alpha helices and libraries thereof In certain embodiments, olefin metathesis reactions are utilized to generate these novel α-helical structures comprising (1) synthesizing a peptide from a selected number of natural or non-natural amino acids, wherein said peptide comprises at least two vinyl amino acids capable of undergoing an olefin metathesis reaction or comprises at least one divinyl amino acid and at least two vinyl amino acids capable of undergoing olefin metathesis reactions; and (2) contacting said peptide with a metathesis catalyst to generate at least one crosslinker and to effect stabilization of an alpha helix structure. In one preferred embodiment, at least two vinyl amino acids are incorporated into the peptide synthesis to generate at least one crosslinker. In another preferred embodiment, at least two vinyl amino acids and at least one divinyl amino acid are incorporated to generate at least two crosslinkers originating from the same amino acid. Alternatively, any combination of divinyl amino acids and vinyl amino acids may be incorporated to generate desired crosslinked structures. It will also be appreciated that in certain embodiments, one or more of either of these crosslinker motifs can be incorporated into a desired stabilized α-helix structure.

In another embodiment, the method of the present invention is utilized to provide stabilized p53 donor helical peptides by incorporating vinyl amino acids into this structural motif and reacting said vinyl amino acids to generate stabilized α-helical structures. Additionally, the present invention provides methods for disrupting the p53/MDM2 binding interaction comprising (1) providing a crosslinker stabilized α-helical structure; and (2) contacting said stabilized α-helical structure with MDM2.

As will be appreciated by one of ordinary skill in the art, in one embodiment, the novel compounds having stabilized secondary structure motifs of the present invention can be synthesized one-at-at time, using traditional peptide synthetic techniques, to generate a particular structural motif In preferred embodiments, however, the these novel stabilized secondary structures are synthesized using combinatorial synthetic techniques, in solution or on the solid support, to generate diverse libraries of novel stabilized compounds having desired secondary structure motifs. Whether using traditional synthetic techniques or combinatorial synthetic techniques, the method of the present invention provides for the generation of compounds having desired stabilized secondary structure motifs that can be based on existing structural motifs or that can represent novel unnatural peptide secondary structure motifs to explore heretofore unknown biological interactions.

Certain preferred embodiments of the novel compound having stabilized secondary structures will be described below; however, this description is not meant to limit the scope of the present invention. Rather, it will be appreciated that all equivalents are intended to be included within the scope of the present invention.

Synthesis of Novel Compounds Having Stabilized Secondary Structure Motifs

As discussed above, the present invention provides novel stabilized compounds having specific secondary structure motifs, libraries thereof, and methods for the preparation of these compounds and libraries thereof. In certain preferred embodiments, the present invention also provides novel α-helix structures, libraries thereof, and methods for the preparation of these α-helices and libraries thereof. Although the following discussion and description of the method of the present invention focuses on alpha helices, it will be appreciated that the methods of the present invention can be applied to generate other peptide secondary structures as well.

Figure 2:
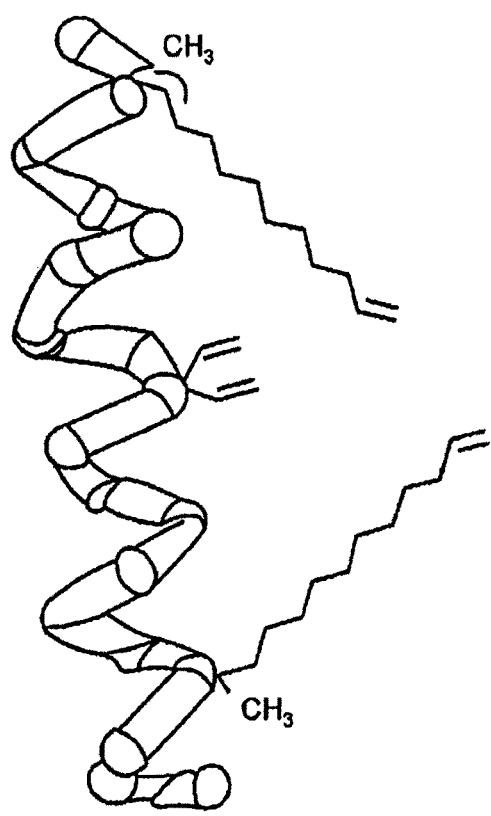
FIG. 2 depicts the installation of a divinyl amino acid for the stabilization of four turns (represented by SEQ ID NO:4).

The synthesis of novel α-helix structures first involves the selection of a desired number of amino acid starting materials. As one of ordinary skill in the art will realize, the number, stereochemistry, and type of amino acid structures (natural or non-natural) selected will depend upon the size of the α-helix to be prepared, the ability of the particular amino acids to generate the α-helix structural motif, and any particular motifs that are desirable to mimic (for example, the p53 donor helical peptide). Furthermore, as mentioned above, for the synthesis of the stabilized alpha helixes, in one preferred embodiment, at least two of the desired amino acids to be utilized in the synthesis are vinyl amino acids capable of undergoing ring closing metathesis reactions to generate at least one stabilizing crosslinker, as shown in FIG. 1. In another preferred embodiment, the peptide to be synthesized incorporates at least two vinyl amino acids and one divinyl amino acid to generate at least two stabilizing crosslinkers originating from the same amino acid moiety, as shown in FIG. 2. It will be appreciated, however, that the number of crosslinking moieties is not limited to one or two, as described above, respectively; rather the number of crosslinking moieties utilized can be varied with the length of the alpha helix as desired, and as compatible with the desired structure to be generated.

Figure 3:
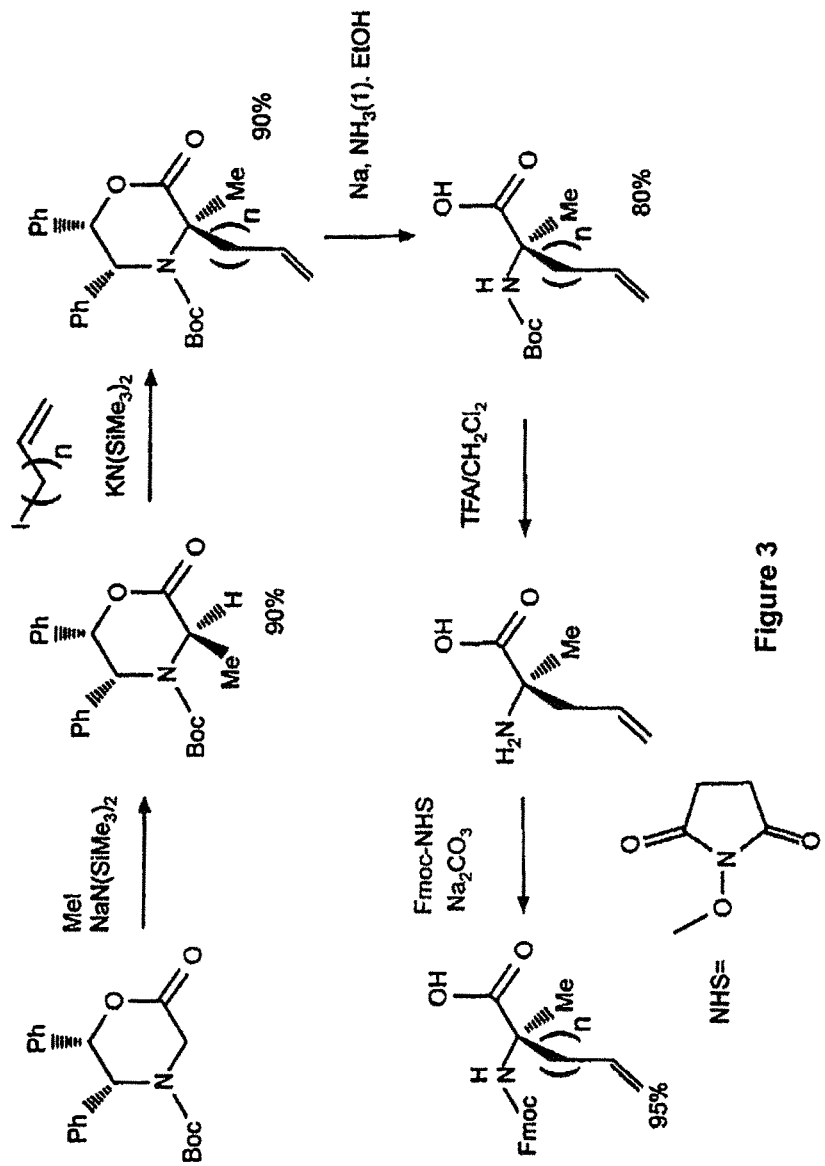
FIG. 3 depicts the synthesis of α-methyl α-alkylolefin amino acids.
Figure 4:
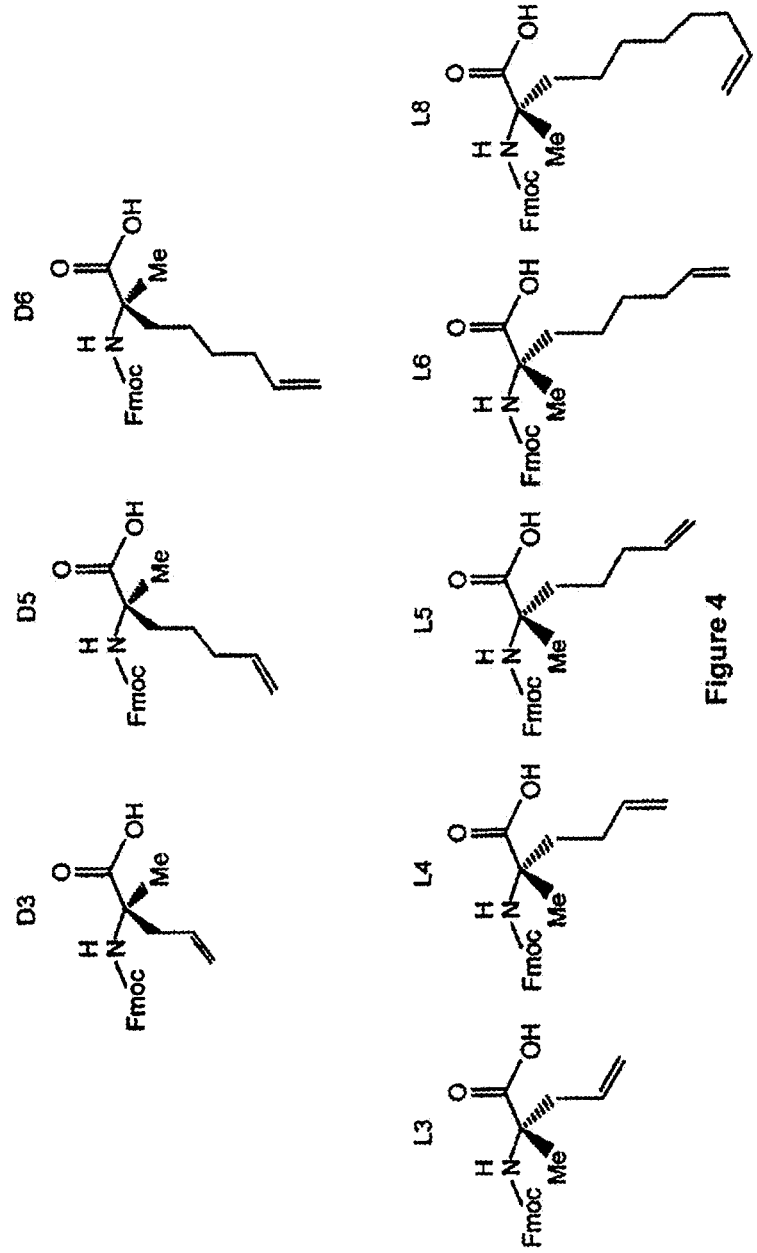
FIG. 4 depicts several different α-methyl α-alkylolefin amino acids for use in the present invention.

In particularly preferred embodiments, α-methyl, α-vinyl amino acids are utilized in the present invention as precursors for crosslinker formation. FIG. 3 depicts a general scheme of the synthesis of α-methyl, α-alkylolefin amino acids. As shown in FIG. 3, commercially available lactone (1) is treated with methyl iodide and sodium tetramethyl disilylazide to generate the methylated lactone (2). Subsequent treatment with a homoallyl iodide in the presence of potassium tetramethyl disilylazide yields the homoallyloxazinone (3). Sodium metal reduction, acid hydrolysis, and protection with Fmoc-NHS generates the protected α-methyl, α-alkylolefin (4) for use in the synthesis of the novel alpha helix structures. As one of ordinary skill in the art will realize, a variety of homoallyl reagents can be utilized to generate amino acids having different lengths of olefin chains. It will also be appreciated that these olefin chains can also be further functionalized with moieties including, but not limited to, branched or linear alkyl moieties, hydroxyl moieties, thiol moieties, amines, carboxyl moieties and substituted or unsubstituted aryl moieties, to name a few. FIG. 4 also depicts certain preferred α-methyl, α-alkylolefin amino acids for use in the present invention having different olefin chain lengths.

Figure 5:
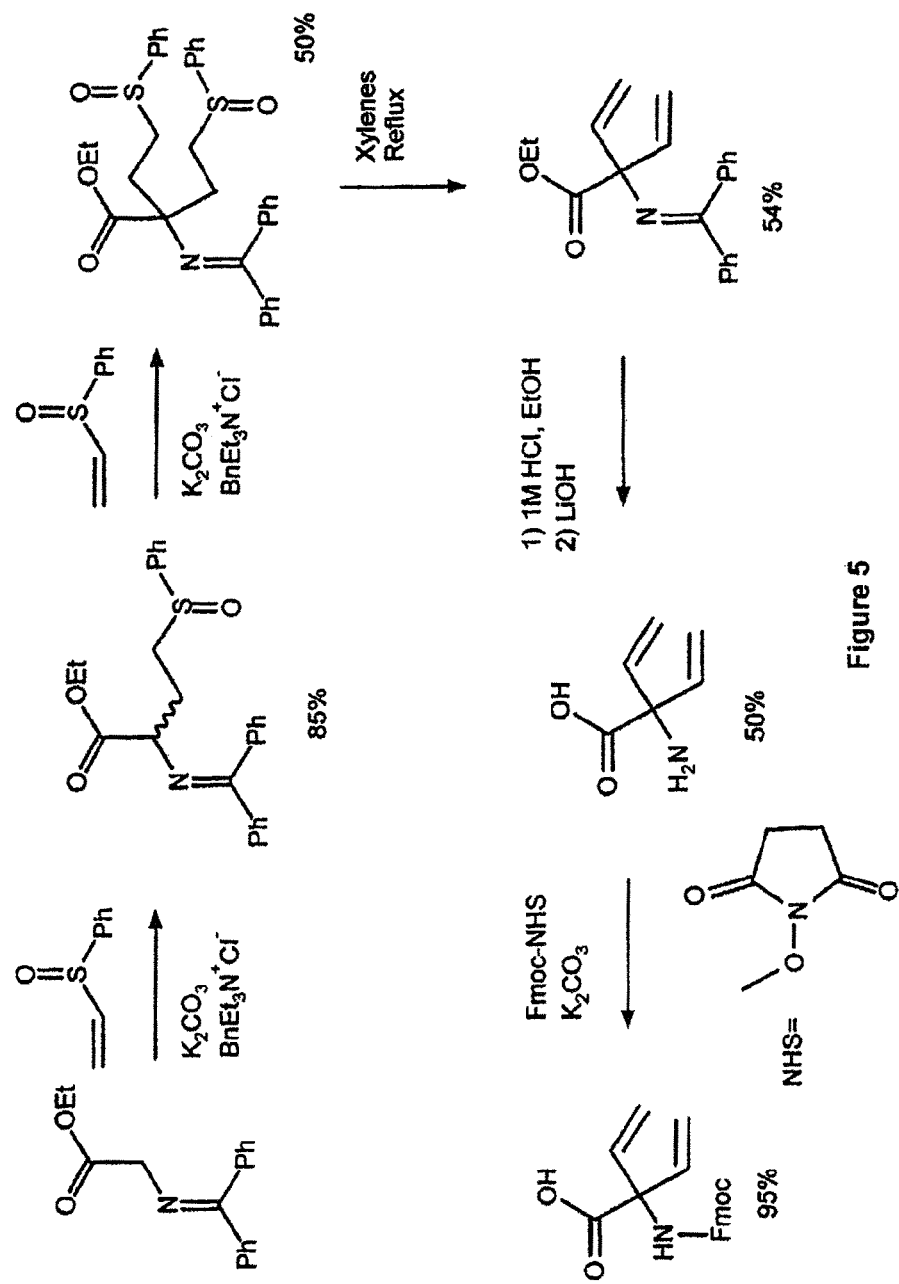
FIG. 5 depicts the synthesis of an Fmoc protected divinyl amino acid.

As discussed above, the novel α-helices of the present invention may also contain two crosslinking units originating from one amino acid. This is facilitated by the synthesis of a divinyl amino acid, from which two olefin metathesis reactions can originate, and is preferably incorporated into the desired peptide synthesis. FIG. 5 depicts the synthesis of an Fmoc protected divinyl amino acid. As shown in FIG. 5, reaction of diphenyliminoglycine (1) sequentially with two equivalents of phenylvinylsulfoxide (2) generates a bis phenylsulfoxide (3), which, upon treatment with xylenes under reflux conditions, eliminates to yield the divinyl moiety (4). Subsequent saponification, acid hydrolysis and deprotection yields the unprotected divinyl glycine moiety (5). Finally, protection with Fmoc-NHS at room temperature yields the protected divinyl glycine moiety (6) for use in the synthesis of the novel α-helix structures of the present invention.

Although vinyl amino acids and divinyl amino acids are preferably utilized to generate the preferred crosslinking moieties as discussed above using ring closing metathesis reactions, the other amino acids utilized in the peptide synthesis may be selected from any standard or nonstandard amino acids. The standard amino acids include Glycine, Alanine, Valine, Leucine, Isoleucine, Proline, Phenylalanine, Tryptophan, Methionine, Serine, Threonine, Cysteine, Tyrosine, Asparagine, Glutamine, Aspartic acid, Glutamic acid, Lysine, Arginine and Histidine. There are over 700 known nonstandard amino acids any of which may be included in the peptide precursors for use in the present invention. See, for example, S. Hunt, The Non-Protein Amino Acids: In Chemistry and Biochemistry of the Amino Acids, edited by G. C. Barrett, Chapman and hall, 1985. Some examples of non-standard amino acids are β-alanine, D-alanine, 4-hydroxyproline, desmosine, D-glutamic acid, γ-aminobutyric acid, β-cyanoalanine, norvaline, 4-(E)-butenyl-4(R)-methyl-N-methyl-L-threonine, N-methyl-L-leucine, and statine. Additionally, the amino acids suitable for use in the present invention may be derivatized to include amino acid residues that are hydroxylated, phosphorylated, sulfonated, and glycosylated, to name a few. Additionally, these amino acids may include functional groups including, but not limited to alcohol, thiol, ketone, aldehyde, ester, ether, amine, imine, amide, nitro acid, carboxylic acid, disulfide, carbonate, carboalkoxy acid, isocyanate, carbodiimide, carboalkoxy and halogen functional groups. It will be appreciated by one of ordinary skill in the art, however, that certain amino acids are capable of promoting formation of alpha helix structures or other desired secondary structures, and thus these specific amino acids are particularly preferred for use in the present invention, depending on the desired secondary structure to be generated. For a detailed discussion of helix propensities studied in various substitution experiments, see Scholtz and Baldwin, the entire contents of which are incorporated herein by reference. Furthermore, as discussed above, it may be desirable to mimic an existing peptide α-helical structure, or other secondary structure, having the crosslinking moiety incorporated therein according to the method of the present invention.

Once the desired amino acids are selected for the synthesis of a desired peptide according to the present invention, synthesis of the desired peptide can be achieved using standard deprotection and coupling reactions. One example of a preferred solution phase peptide synthesis coupling protocol includes the use of N, N-dicyclohexylcarbodiimide (DCC)/1-hydroxybenzotriazole (HOBT) as a peptide coupling agent (see, M. Bordansky, Petpide Chemistry, Springer Verlag, N.Y., 1988, pp. 55-146 the entire contents of which are incorporated herein by reference). Other peptide synthesis techniques have been extensively discussed in "Bioorganic Chemistry" as cited herein. One of ordinary skill in the art will realize that the choice of a particular synthetic technique will depend upon the particular structures to be synthesized.

After a desired peptide is synthesized using an appropriate technique, the peptide is contacted with a specific reagent to promote carbon-carbon bond formation. In one particular embodiment, a metathesis catalyst is utilized to effect one or more olefin metathesis reactions and subsequent generation of a crosslinker and stabilization of the alpha helix or other desired secondary structure. One of ordinary skill in the art will realize that a variety of metathesis catalysts can be utilized in the present invention. Selection of a particular catalyst will vary with the reaction conditions utilized and the functional groups present in the particular peptide. Exemplary catalysts include, but are not limited to stabilized, late transition metal carbene complex catalysts such as Group VIII transition metal carbene catalysts, most preferably Ru and Os metal centers having a +2 oxidation state, an electron count of 16 and pentacoordinated. One of ordinary skill in the art will realize that other appropriate olefin metathesis catalysts may be utilized. For an excellent discussion of metathesis reactions, see, Grubbs et al., "Ring Closing Metathesis and Related Processes in Organic Synthesis" *Acc. Chem. Res.* 1995, 28, 446-452, and U.S. Pat. No. 5,811,515.

It will also be appreciated, that in addition to olefin metathesis catalysts, other reagents capable of promoting carbon-carbon bond formation can also be utilized. For example, other reactions that can be utilized, include, but are not limited to palladium coupling reactions, transition metal catalyzed cross coupling reactions, pinacol couplings (terminal aldehydes), hydrozirconation (terminal alkynes), nucleophilic addition reactions, and NHK (Nozaki-Hiyama-Kishi (Fürstner et al., *J. Am. Chem. Soc.* 1996, 118, 12349)) coupling reactions. Thus, the appropriate reactive moieties (alkene, alkyne, aldehyde etc.) are first incorporated into desired amino acids or unnatural amino acids (see vinyl amino acid synthesis for one example), and then the peptide is subjected to reaction conditions to effect carbon-carbon bond formation which results in the formation of a crosslinker and subsequent stabilization of a desired secondary structure.

Figure 6:
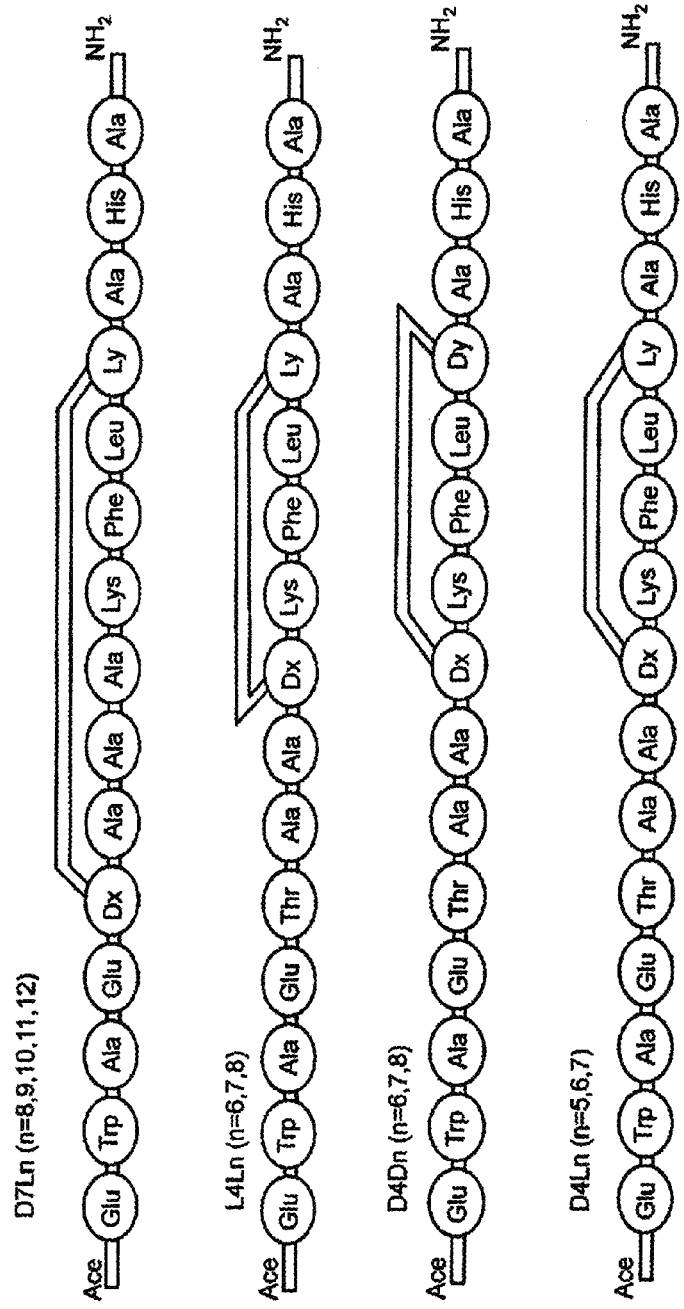
FIG. 6 depicts several different stabilized α-helix structures of the present invention (wherein D7Ln is represented by SEQ ID NO:2, and L4Ln, D4Dn, and D4Ln, are represented by SEQ ID NO:3).
Figure 6A:
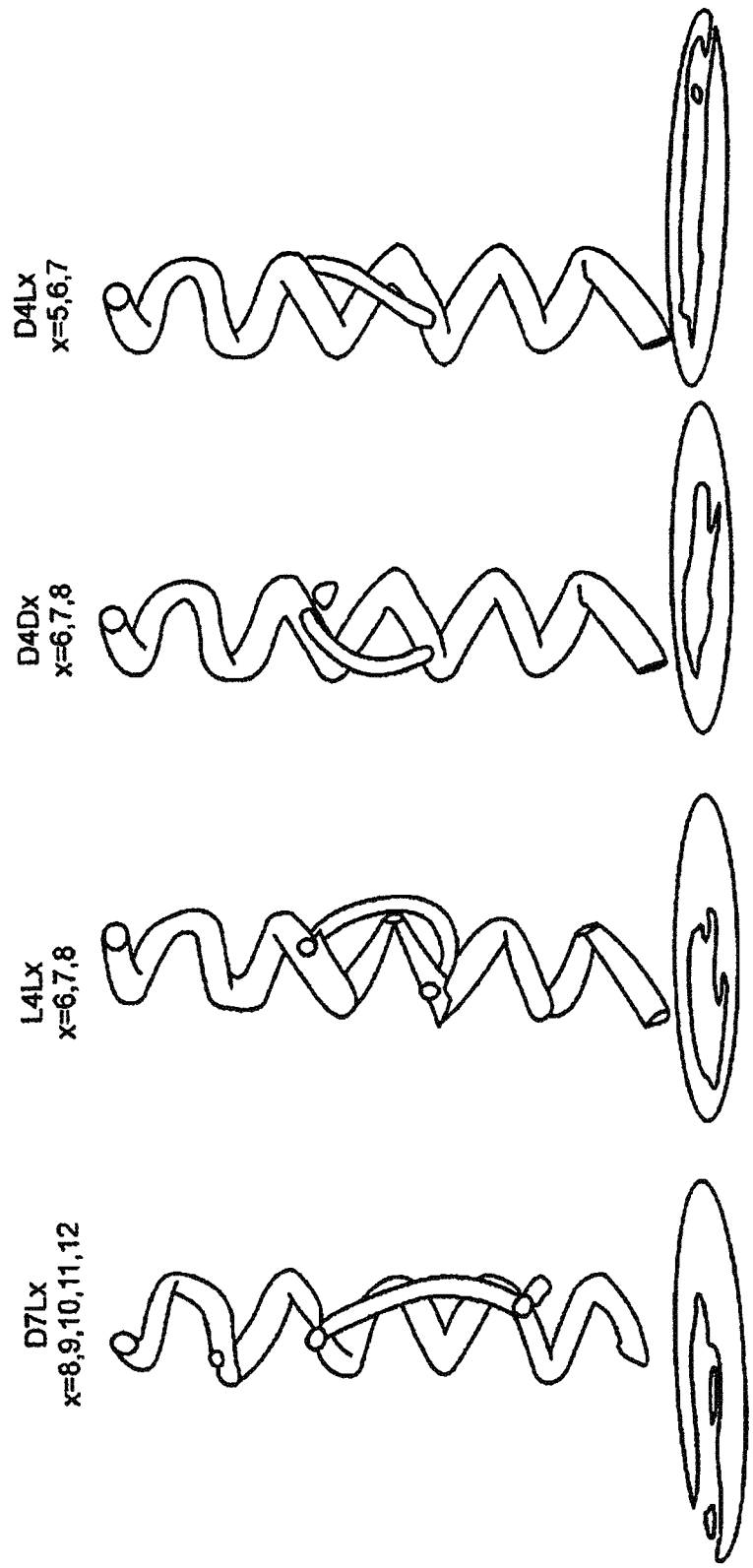
FIG. 6A depicts experimental determination of exemplary helix stabilizers.
Figure 7:
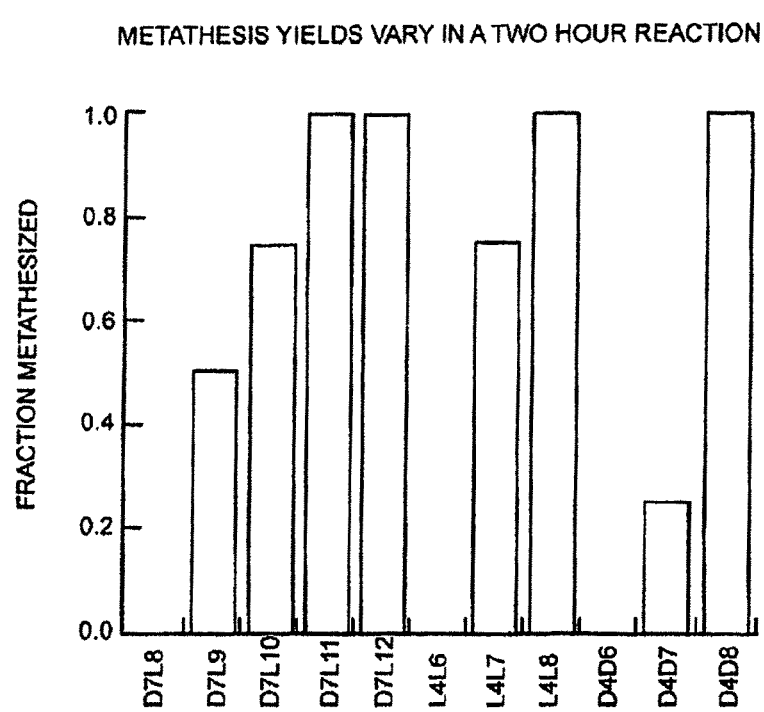
FIG. 7 depicts variations in metathesis yields in a two hour reaction.
Figure 8:
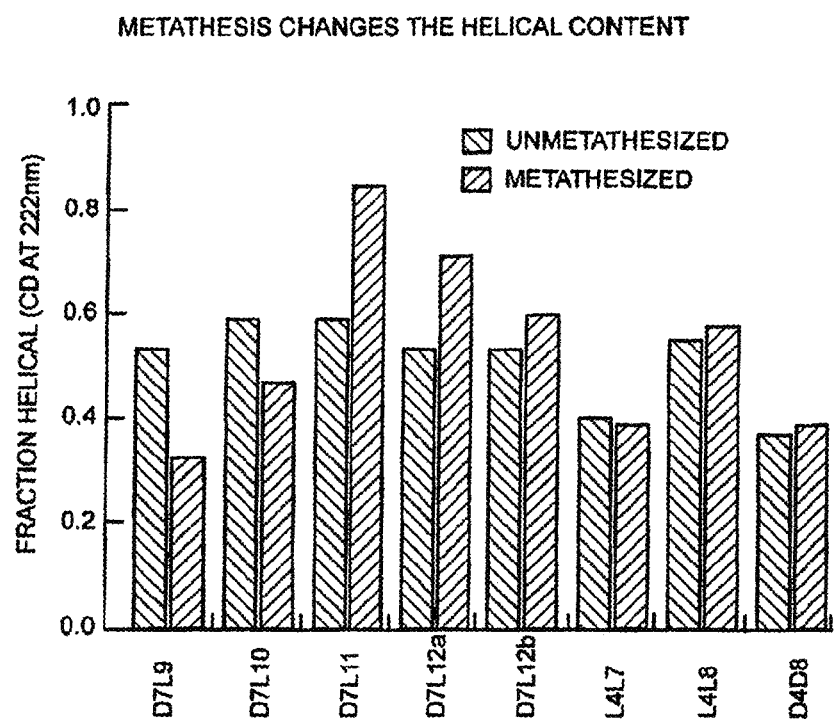
FIG. 8 depicts a graph showing a summary of α-helicity and metathesis percentages.
Figure 9:
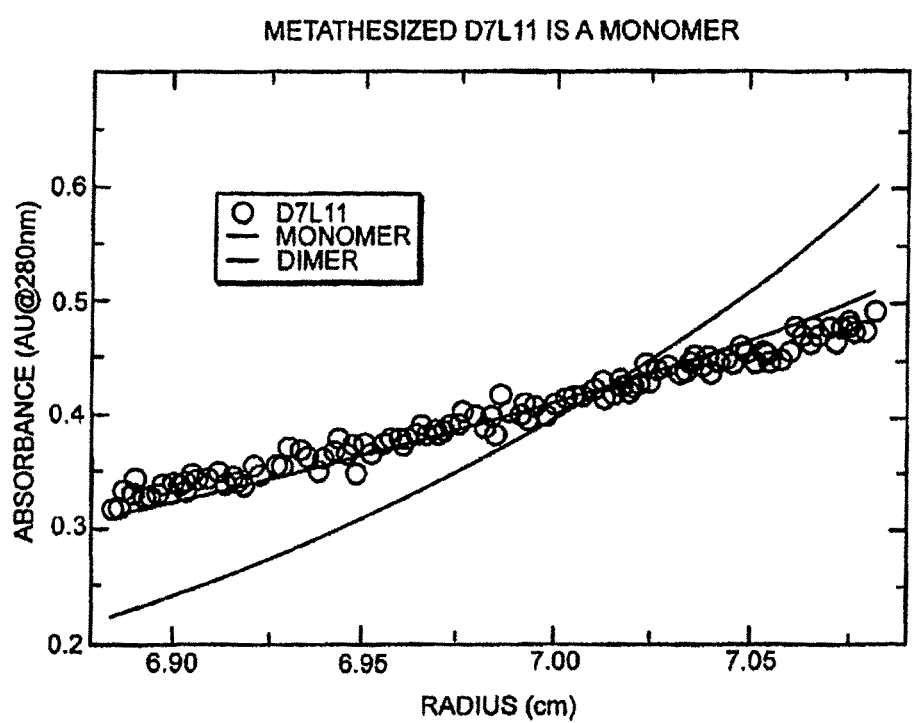
FIG. 9 depicts results showing that metathesized D7L11 is a monomer.

In a particularly preferred embodiment of the present invention, the method of the present invention was utilized to engineer stabilized alpha helical peptides that are capable of binding tightly to a helix acceptor and disrupting native protein/protein interactions. Towards this end, two alpha-methyl, alpha-alkyl terminal olefin unnatural amino acids, were incorporated into the peptide fragment that forms the donor helix in the native complex (p53) and cross-linking the amino acids using a ruthenium metathesis catalyst to form a bridge that stabilizes the peptide in an alpha helical conformation. Using this approach, 14 different model peptides (as shown in FIG. 6), incorporating different stereochemistry, vinyl amino acid placements and carbon chain lengths, were synthesized to explore the different ways of stabilizing the helix. Each of these were characterized by circular dichroism spectroscopy to determine the stabilization in an alpha helical conformation. FIG. 6A also depicts the experimental determination of the best helix stabilizer. FIG. 7 depicts the variation in the metathesis yields in a two hour reaction. As shown in FIG. 8, the % helicity is compared for metathesized and unmetathesized peptides and D7L11 provides the optimal helicity. Thus, it is particularly preferred to generate a structure having a cross link from residue (i) to residue (i+7) with (S) stereochemistry at the alpha carbon of residue (i) and (R) stereochemistry at position (i+7). It is also particularly preferred that the number of carbons in the crosslinker is eleven. As shown in FIG. 8, helix stabilizing cross-linker caused the model peptide to exhibit almost 90% helicity in water. FIG. 9 additionally shows that metathesized D7L11 is a monomer.

Figure 10:
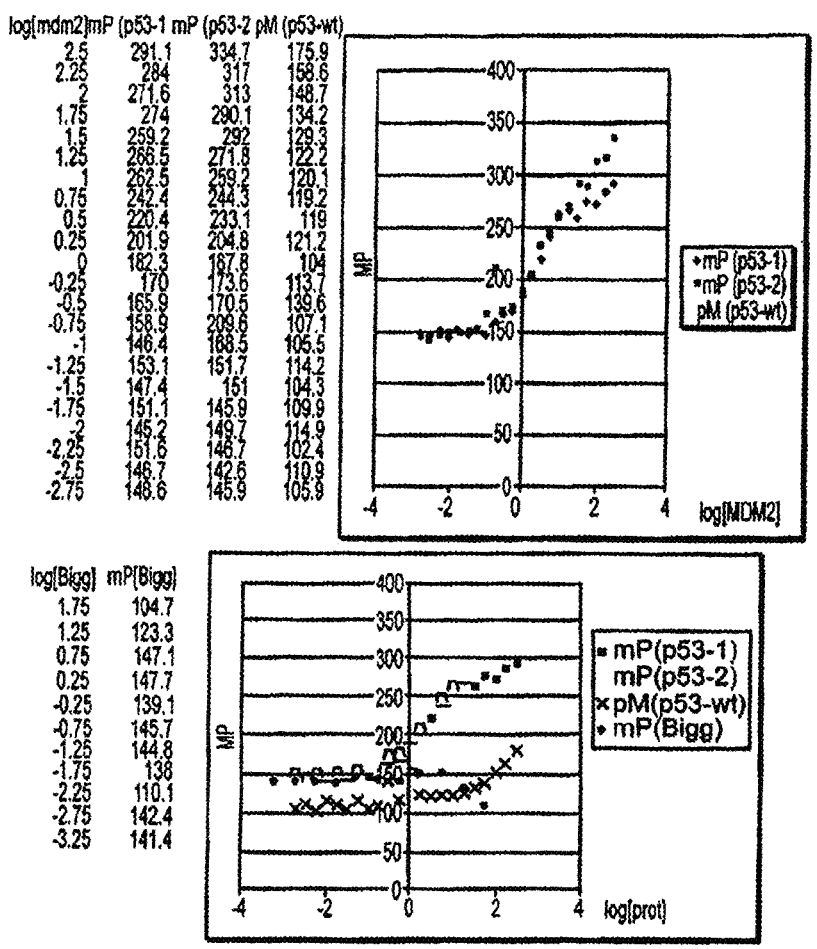
FIG. 10 depicts a fluorescence polarization binding study of p53 peptides with MDM2.

As an example of the utility of these novel stabilized alpha helix structures, this preferred alpha helix structure was implemented in the p53/MDM2 system by synthesizing two stabilized p53 donor helical peptides and determining their binding to the Xenopus MDM2 protein. The unnatural amino acids are incorporated into the p53 donor fragment on the side of the helix that does not interact with MDM2 so as not to disrupt the evolved p53/MDM2 binding interface. Preliminary fluorescence polarization results, as depicted in FIG. 10, show that both stabilized p53 peptides begin to bind MDM2 at 100 fold lower MDM2 concentration, and thus 100 fold tighter, than the native p53 donor fragment.

Figure 11:
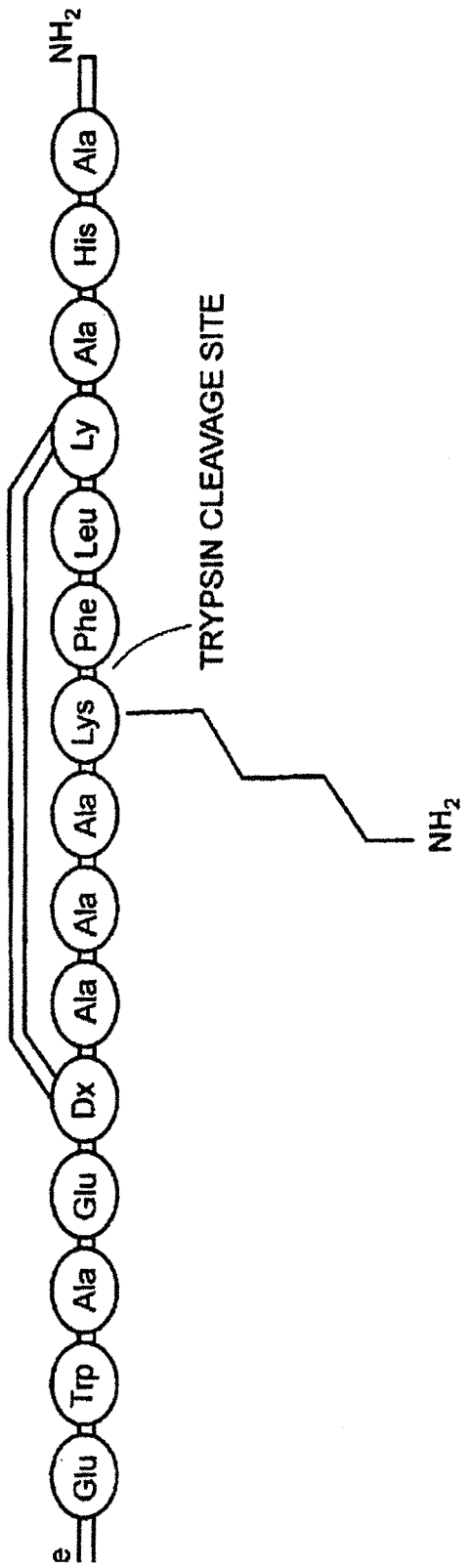
FIG. 11 depicts the model peptide as a substrate for the protease trypsin (represented by SEQ ID NO:2).
Figure 12:
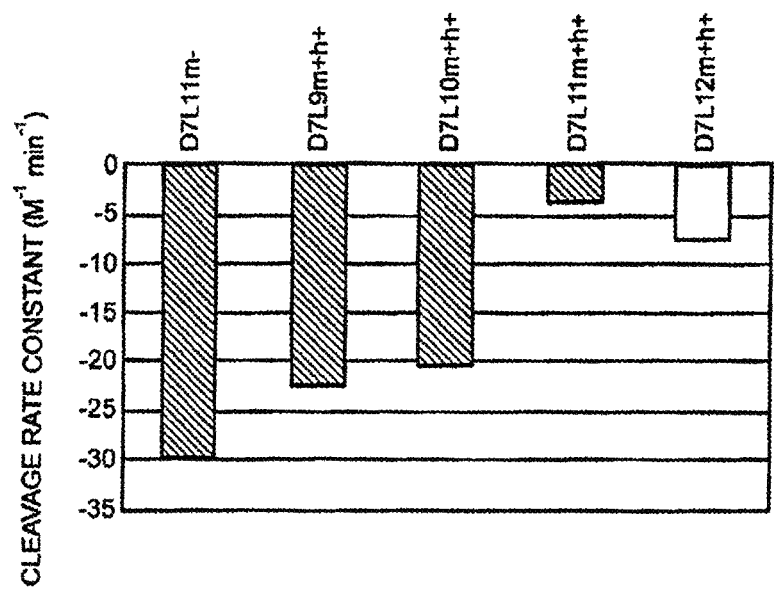
FIG. 12 depicts rates of Trypsin cleavage.
Figure 13:
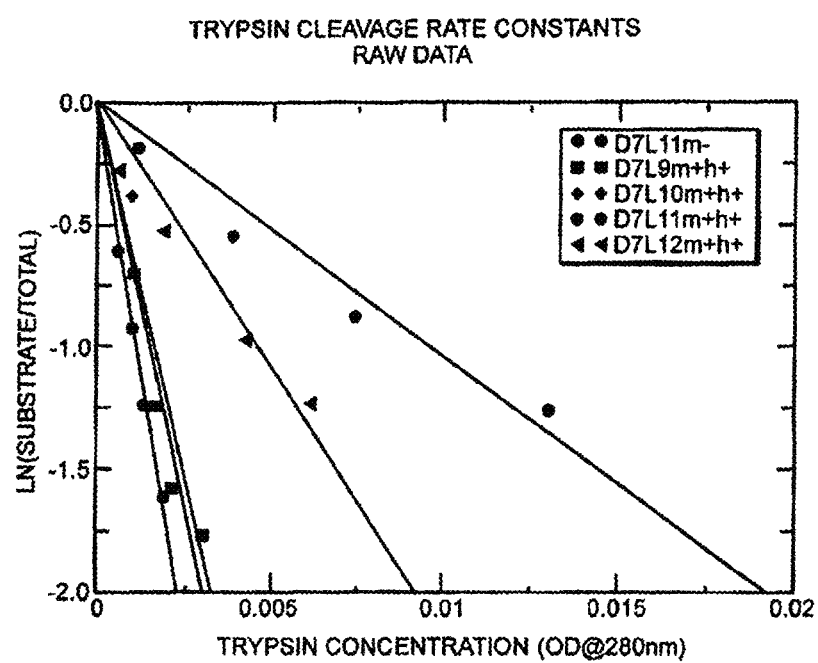
FIG. 13 depicts raw data for trypsin cleavage rate constants.
Figure 14A:
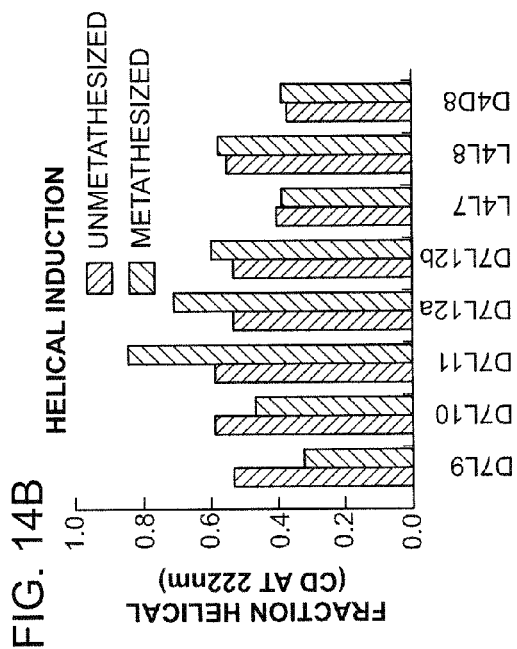
FIG. 14A depicts variations in metathesis yields in a two-hour reaction.
Figure 14B:
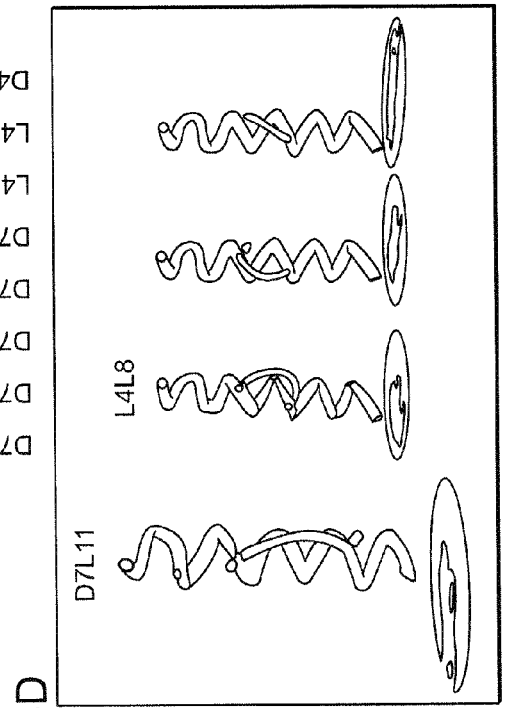
FIG. 14B depicts a graph showing a summary of α-helicity and methathesis percentages.
Figure 14C:
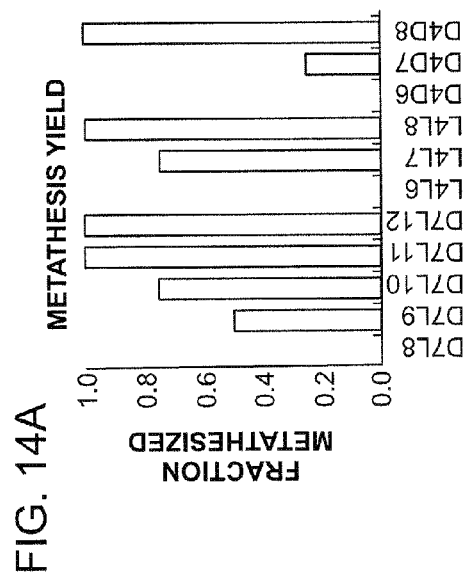
FIG. 14C depicts rates of Trypsin cleavage.
Figure 14D:
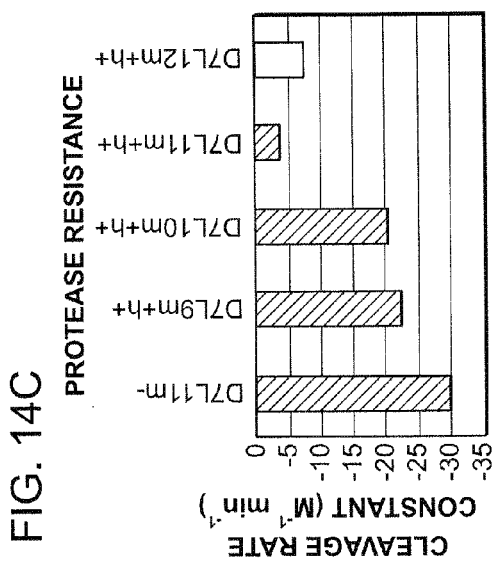
FIG. 14D depicts experimental determination of exemplary helix stabilizers.

Additionally, FIG. 11 shows that the model peptide is a substrate for the protease trypsin. As depicted in FIGS. 12, 13, and 14, an inventive stabilized compound D7L11 shows the slowest rate of trypsin cleavage, and thus is an exemplary helix stabilizer.

Combinatorial Synthesis of Novel Stabilized Structures

It will also be appreciated by one of ordinary skill in the art that the method described above can also be applied to combinatorial synthesis of the novel stabilized structures having desired secondary structures. Although combinatorial synthesis techniques can be applied in solution, it is particularly preferred that combinatorial techniques are performed on the solid phase using split-and-pool techniques. In general, in a preferred method of the present invention, Solid Phase Peptide Synthesis (SPPS) techniques are utilized. Similarly to solution phase techniques, in solid phase techniques, the choice of the protecting groups must be considered, as well as the specific coupling techniques to be utilized. For a detailed discussion of peptide synthesis techniques for solution phase and solid phase reactions, see, Hecht, ed. "Bioorganic chemistry: Peptides and Proteins, Oxford University Press, New York: 1998, the entire contents of which are incorporated herein by reference.

The present invention, in one aspect, provides methods for the synthesis of libraries of novel stabilized compounds having secondary structure motifs comprising (1) providing a collection of resin-bound amino acids; (2) deprotecting each of said resin bound amino acids; (3) separating said collection of deprotected resin bound amino acids into n equal portions, wherein n represents the number of different types of amino acids to be coupled; (4) coupling of each of n types of amino acids to the deprotected amino acid; (5) combining each of the n portions together; (6) repeating steps (2)-(5) until a desired peptide is obtained, wherein at least two of the amino acids coupled at any step comprise substituted or unsubstituted vinyl amino acids capable of undergoing ring closing metathesis reaction, or wherein at least one amino acid coupled at any step comprises a substituted or unsubstituted divinyl amino acid and at least two of the amino acids incorporated at any step comprise substituted or unsubstituted vinyl amino acids, whereby said divinyl amino acid and said vinyl amino acid are capable of undergoing ring closing metathesis reactions to generate two cross-linkers originating from the same amino acid; and (7) contacting said peptide with a ring closing metathesis catalyst to generate a library of cross-linked stabilized α-helix peptide structures. During the course of the combinatorial synthesis, various parameters can be varied, including, but not limited to vinyl and divinyl amino acid placement, stereochemistry of amino acids, vinyl and divinyl chain length and functionality and amino acid residues utilized. Furthermore, as discussed above, other reactive moieties (such as aldehydes or alkynes, to name a few) can be utilized instead of alkene moieties and thus other carbon-carbon bond forming reactions can be utilized to form stabilized compounds having secondary structure motifs and are within the scope of the present invention.

It will be appreciated by one of ordinary skill in the art that the libraries of compounds having stabilized secondary structures can be further diversified at specific functional moieties after the desired stabilized structures are formed. For example, free or latent amino acid functionalities may be diversified, or alternatively or additionally, free or latent functionality present on the cross-linkers may be diversified. In particularly preferred embodiments, in but one example, the hydrophobicity of stabilized structures may be increased by the introduction of hydroxyl moieties. As one of ordinary skill in the art will realize, the diversification reactions will be selected to introduce functionalities compatible with the particular stabilized structures and the desired biological interactions, and these functionalities include, but are not limited to hydrogen, alkyl, aryl, phenoxy, methoxy, halide, benzene, heteroaryl, carboxyl, carboxalkyl, carboxaryl, arylalkyl, thio and hydroxyl.

Uses of the Novel Stabilized Structures of the Present Invention

The novel stabilized structures, libraries, and methods for making said novel stabilized structures of the present invention can be utilized in various disciplines. Any available method may be employed to screen the libraries produced according to the present invention to identify those with desirable characteristics for a selected application.

To give just a few examples, the present invention can be used to produce novel stabilized structures that control (i.e., promote or inhibit) cell functions. Such compounds may be formulated and utilized as therapeutic pharmaceuticals. For example, such therapeutic pharmaceuticals, through interactions with cellular receptors, can control cell proliferation, viral replication, gene expression, or any other cell signaling process.

Figure 15:
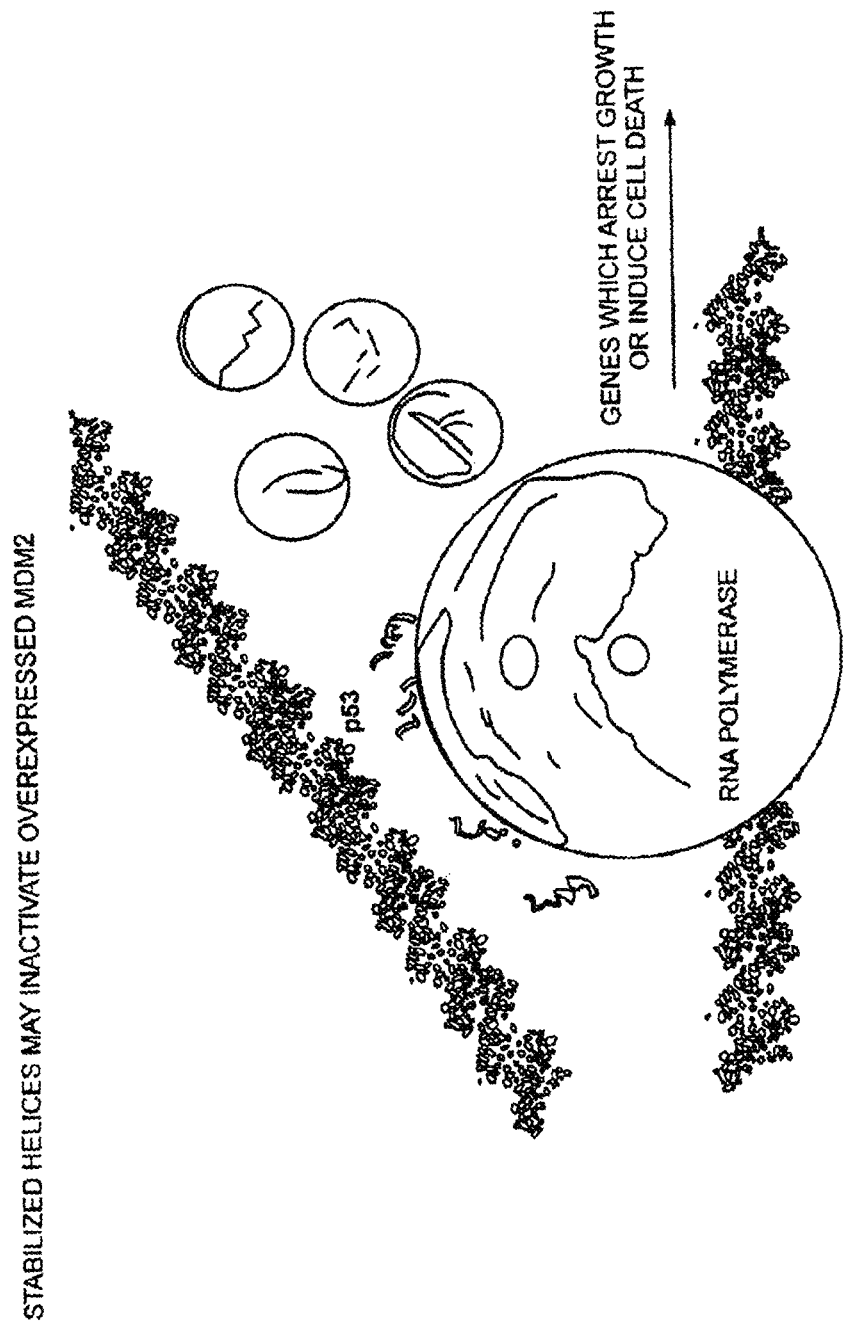
FIG. 15 depicts that stabilized helices may inactivate overexpressed MDM2.
Figure 16:
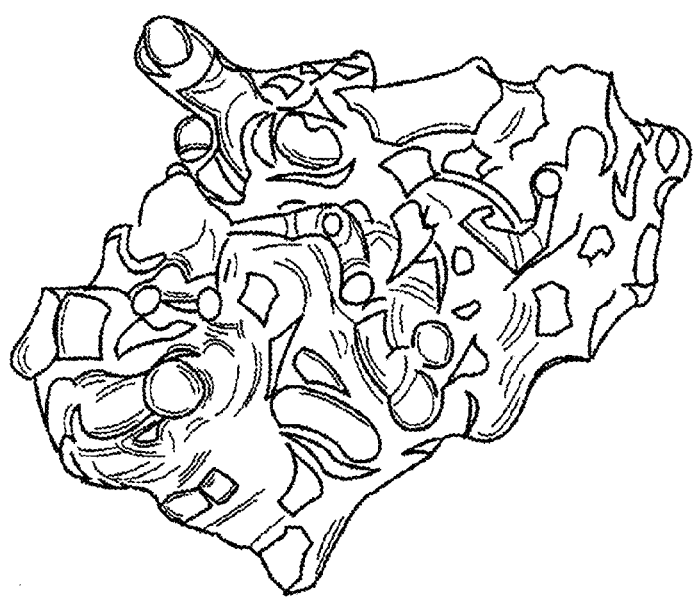
FIG. 16 depicts exemplary stabilized compounds for use in the P53/Mdm2. P53-wt is represented as SEQ ID NO:10, P53-1 is represented by SEQ ID NO:11, and P53-2 is represented by SEQ ID NO:12.
Figure 17:
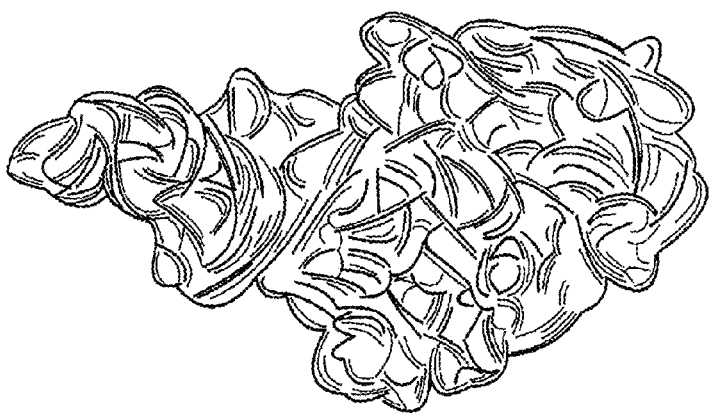
FIG. 17 depicts exemplary stabilized compounds for use in the Bak/Bcl-xL system. Bak-wt is represented as SEQ ID NO:5, Bak-1 is represented by SEQ ID NO:6, Bak-2 is represented by SEQ ID NO:7, Bak-3 is represented by SEQ ID NO:8, and Bak-4 is represented by SEQ ID NO:9.
Figure 18:
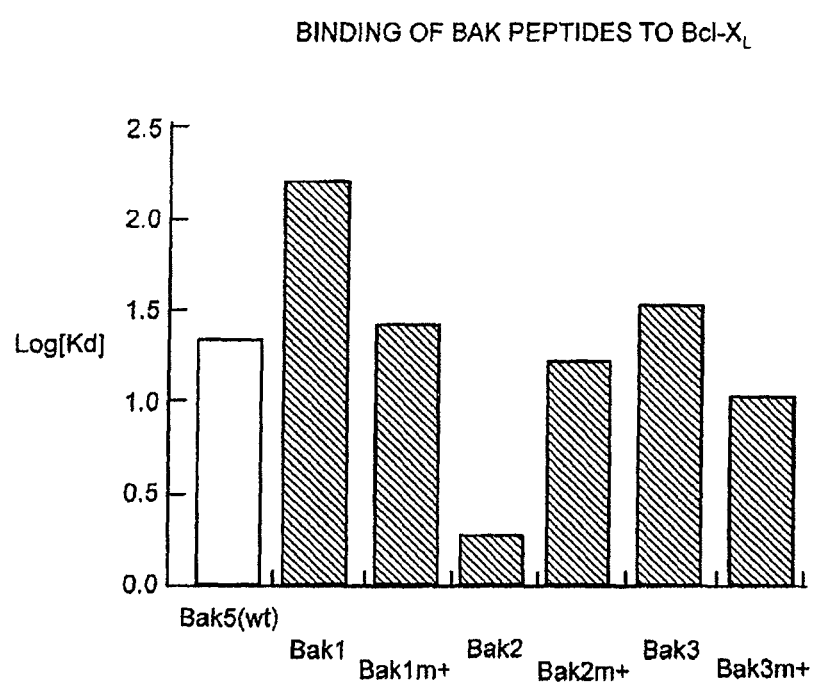
FIG. 18 depicts the binding of Bak peptides to Bcl-$x_L$.

More specifically, as mentioned above, many biologically important protein/protein interactions, such as p53/MDM2 (see FIGS. 15 and 16) and Bcl-X1/Bak (see FIGS. 17 and 18) are mediated by one protein donating a helix into a cleft of its helix-accepting partner. The interaction of p53 and MDM2 has been discussed in detail (see, Shair "A Closer View of an Oncoprotein-tumor Suppressor Interaction, *Chem. & Biol.* 1997, 4, 791, the entire contents of which are incorporated herein by reference) and mutations in the p53 gene have been identified in virtually half of all reported cancer cases. As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic α-helix of 2.5 turns that inserts into the MDM2 crevice. Thus, novel alpha helix structures generated by the method of the present invention can be engineered to generate structures that may bind tightly to the helix acceptor and disrupt native protein-protein interactions. These structures may then be screened using high throughput techniques to identify optimal small molecule peptides. The novel structures that disrupt the MDM2 interaction might be useful for many applications, including, but not limited to, control of soft tissue sarcomas (which overexpresses MDM2 in the presence of wild type p53). These cancers may be held in check with small molecules that could intercept MDM2, thereby preventing suppression of p53. Additionally, small molecules disrupters of MDM2-p53 interactions could be used as adjuvant therapy to help control and modulate the extent of the p53 dependent apoptosis response in conventional chemotherapy. FIG. 15 shows that stabilized helices may inactivate overexpressed MDM2 and FIG. 16 depicts novel stabilized structures to be utilized for the P53/Mdm2 system. Similarly, FIG. 17 depicts novel stabilized structures utilized for the Bak/Bcl-$x_L$ system and FIG. 18 depicts the binding of Bak peptides to Bcl-$x_L$.

In addition to the abovementioned uses, the inventive stabilized structures can be used for studies in bioinorganic chemistry or in catalysis, either as a ligand for a transition metal capable of mimicking an important biological environment, or by acting in concert with a particular transition metal catalyst to effect a desired chemical reaction.

Furthermore, the inventive stabilized structures are also useful in the area of materials science. For example, molecules such as lipids and other polymeric molecules may be attached to the terminal peptide moieties and thus generate potentially important biomaterials.

It will be appreciated by one of ordinary skill in the art that the present invention is not intended to be limited to the abovementioned uses, but rather may be employed in many suitable contexts and disciplines.

Peptides are excellent protein ligands, both for their tight binding and for the ease by which can be discovered using diversity based techniques. On the other hand, peptides are poor therapeutics because of their low membrane permeability and susceptibility to protease cleavage. To enhance the bioavailability of short α-helical peptides, we have developed a chemical system wherein all-hydrocarbon covalent crosslinks are installed across one and two turns of an α-helix using olefin metathesis chemistry. By screening crosslinker position, stereochemistry and crosslinker length, we have determined the optimal crosslinking geometry for maximum metathesis yield and maximum helix-stabilization in a model system. The installation of this optimal crosslink system enhances the helix content of a model peptide from 41% to 85%, which is comparable to the best helix enhancement seen in other systems. Installation of this crosslink system also enhances resistance to trypsin cleavage by over 40-fold when compared to the unmodified control peptide.

Peptides that bind macromolecular receptors in an extended conformation can often be converted to mimetics that retain binding but have improved protease resistance and membrane permeability[1]. However, peptides that must fold upon themselves in order to bind a receptor have proven difficult to improve by similar approaches, because of their larger size and the difficulty of mimicking functionality presented on a complex folded molecular surface. One such folded peptide structure that participates widely in biomolecular recognition events is the α-helix[2,3]. Most peptides that bind their receptors in an α-helical conformation have little helical structure when free in solution. Stabilizing the helical form of such peptides is thus expected to favor receptor binding by virtue of preorganization. Furthermore, the intramolecular hydrogen bonding associated with helix formation reduces the exposure of the polar amide backbone, thereby reducing the barrier to membrane penetration and increasing the resistance to protease cleavage.

A number of approaches for covalent helix-stabilization have been reported[4], but most involve crosslinks that are both polar and pharmacologically labile, such as disulfides[5] and lactam bridges[6,7]. An important conceptual advance on this front is the development by Grubbs and co-workers of chemistry for olefinic crosslinking of helices through O-allyl serine residues located on adjacent helical turns, via ruthenium-catalyzed ring closing metathesis (RCM)[8]. The particular crosslinks analyzed in that study, however, showed no evidence of enhancing helical stability, highlighting the difficulty of this problem from a design standpoint. Here we have taken an alternate metathesis-based approach, namely to screen multiple configurations of all-hydrocarbon crosslinks differing in position of attachment, stereochemistry, and crosslinker length. Where some configurations impart significant helix-stabilization, others actually destabilize the helix. We show that stabilizing an α-helix in this way leads to markedly increased resistance to proteolysis.

Figure 19:
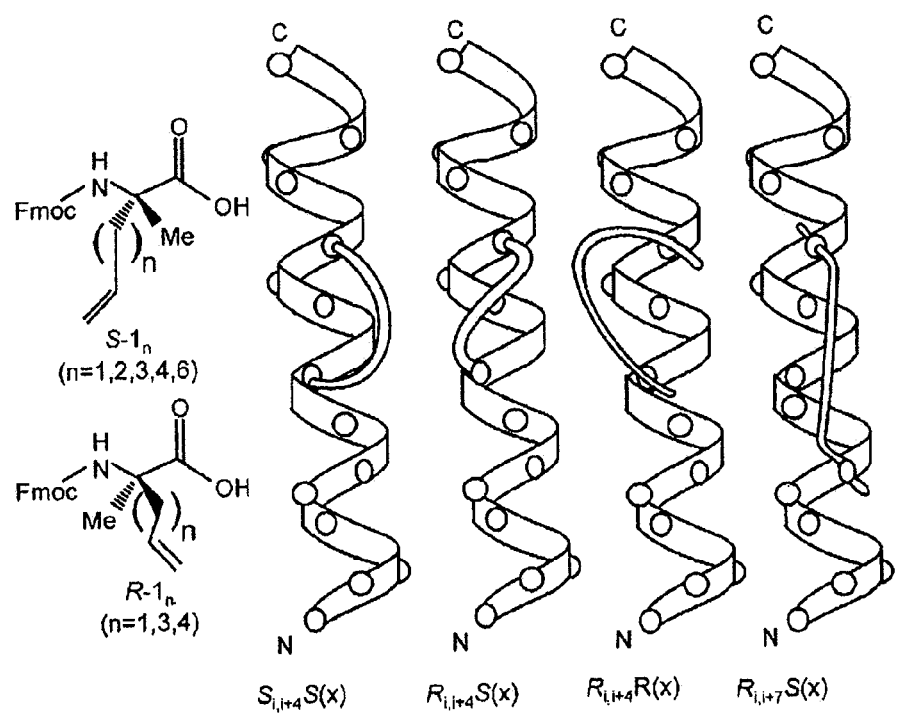
FIG. 19 depicts a strategy for stabilizing α-helices through an all-hydrocarbon crosslinking system. The key components of the system are α-methylated amino acids 1, bearing olefinic side-chains of varying length and configured with either R or S stereochemistry. These are incorporated into peptides at the i and either i+4 or i+7 position, and then connected via olefin metathesis to crosslink one or two turns, respectively, of the helix. The overall side-chain length of 1=n+2, and of the crosslinks=n+n+2. The nomenclature Ri,i+7S(11) refers to a peptide with an R and an S configured amino acid at positions "i", and "i+7" respectively, and 11 carbons in the metathesized crosslink.

The actual structure of crosslinks positioned on one face of an α-helix is very dependent upon the stereochemistry at the attachment points (FIG. 19). We therefore designed unnatural amino acids 1 having either R or S stereochemistry at the α-carbon, and bearing alkyl tethers of various lengths (FIG. 19). To avoid the intrinsic helix-destabilizing effect of D-configured amino acids while capitalizing on the helix-stabilizing effect of α,α-disubstituted amino acids we introduced an α-methyl group into 1. We incorporated these synthetic amino acids across either one or two turns (i and i+4, or i+7 position, respectively; FIG. 19) of the C-peptide sequence from Rnase A[9]; this particular peptide was chosen because it exhibits partial helicity in water, allowing us to observe both increases and decreases in helical content owing to modifications[10].

None of the peptides in the $R_{i,i+4}S(x)$ series (x=5,6,7) underwent metathesis to any measurable extent. In the $R_{i,i+4}R(x)$ series, the peptide having a 6-carbon crosslink (x=6) failed to metathesize, but that having a 7-carbon crosslink (x=7) formed to the extent of 17%, and the metathesis reaction leading to the 8-carbon crosslinked peptide (x=8) went to completion (>98%) (Table 1). In the $S_{i,i+4}S(x)$ series, the shortest member (x=6) again failed to undergo RCM, but the longer versions, x=7 and 8, underwent 68% and >98% conversion, respectively. In the $R_{i,i+7}S(x)$ series the crosslinks were again formed with increasing efficiently as they became longer (x=8, <5%; x=9, 51%; 10, 77%; 11, >98%; 12, >98%). Two general trends are evident from these reactions. First, the conversions by RCM increase as a function of increasing ring size in the macrocyclic crosslink. Indeed, the 34-membered macrocycle in $S_{i,i+7}R(12)$ is formed rapidly and efficiently, despite being one of the largest macrocycles closed by RCM to date[11]. Second, small changes in ring size can cause dramatic effects on the efficiency of crosslinking; for example, the 30-membered macrocycle in $R_{i,i+7}S(8)$ fails to form appreciably, whereas the 31-membered ring of $R_{i,i+7}S(9)$ forms to the extent of 50%. We believe both effects can be explained by templating of the RCM reaction through helix induction of the unmetathesized precursor peptides on the solid support in the solvent dichloroethane. According to this explanation, tethers that are too short to span the gap along the face of the templating helix are not metathesized efficiently.

Figure 20A:
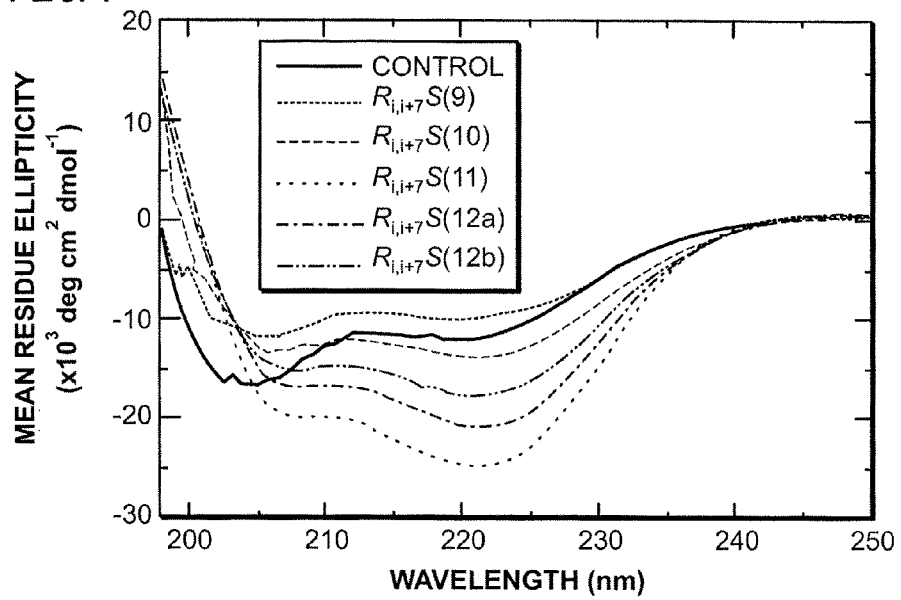
FIG. 20. (A) Different crosslinks destabilize and stabilize the helix to different extents in the Ri,i+7S series. (B) In the Ri,i+7S series α-methyl amino acids increase helical structure by ca. 15%. Inducing a crosslink using olefin metathesis has an effect on helicity that depends on the crosslink length. Ri,i+7S(11) is the best helix stabilizer. The uncertainties in these measurements are no greater than +/−5%.
Figure 20B:
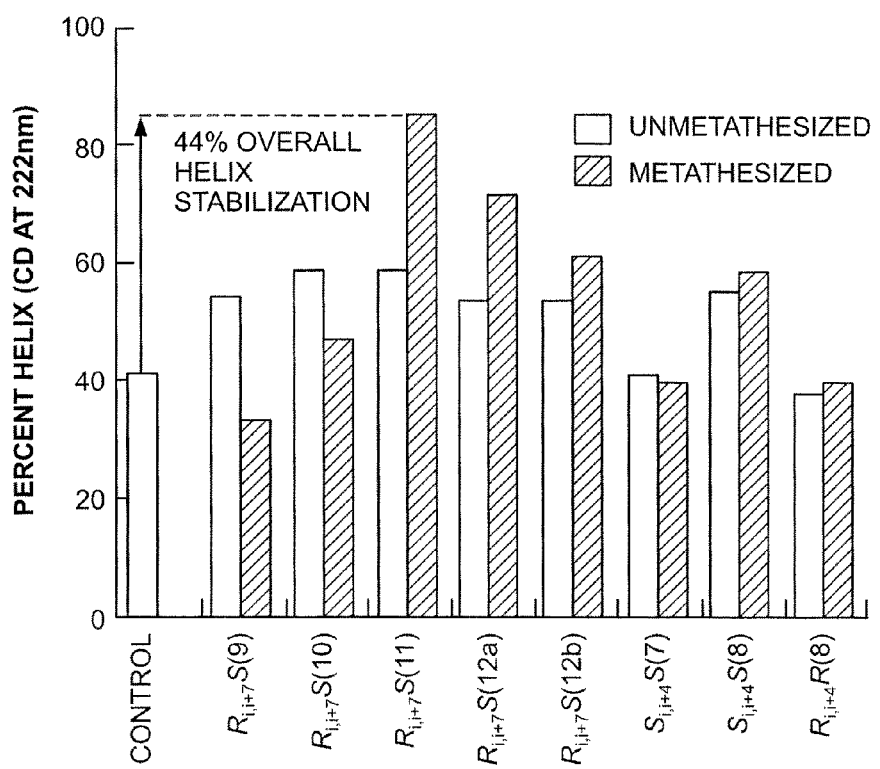
Figure 21:
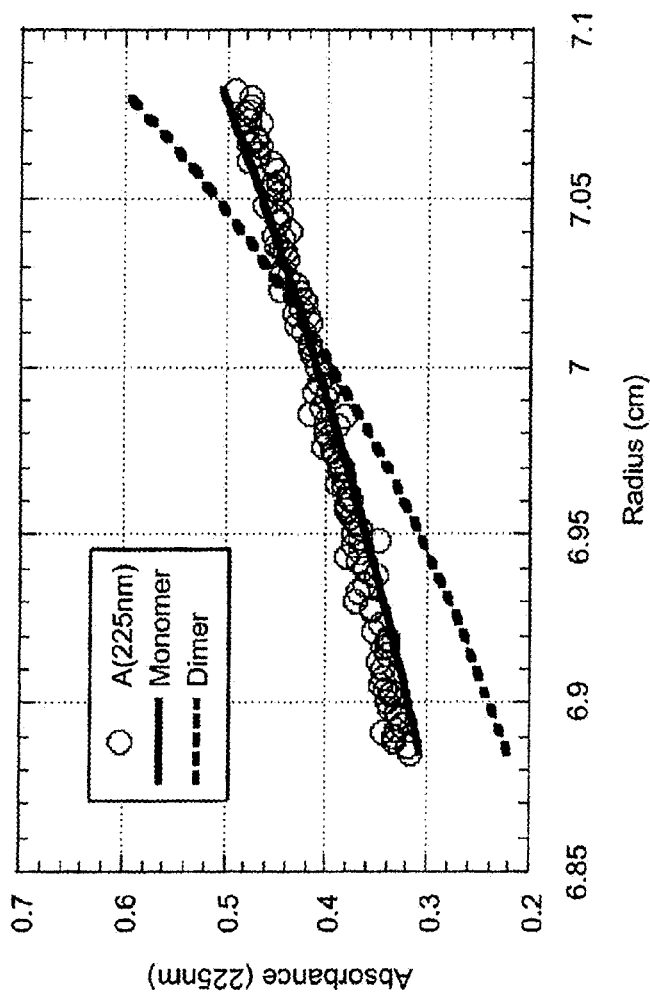
FIG. 21 depicts data relating to the sedimentation equilibrium of Ri,i+7S(11). The graph depicts the experimentally observed absorbance at 225 nm of Ri,i+7S(11) (open circles), the calculated absorbance at 225 nm of a corresponding idealized monomeric peptide (solid line), and the calculated absorbance at 225 nm of a corresponding idealized dimeric peptide (dashed line); all data is presented as a function of the radius of the sample. The experimental data fits the calculated data for the idealized monomeric peptide.

To determine the effect of olefinic crosslinking on the helical propensity of the peptides, we used circular dichroism to provide a quantitative measure of helical content[12] (FIG. 20). As a benchmark, the control unmodified RNase A peptide is ~40% α-helical in water containing 0.1% trifluoroacetic acid at 4° C. All peptides that underwent RCM to the extent of ~50% or more were measured in both uncrosslinked and crosslinked forms. In most cases, and as expected[13], inclusion of the two α,α-disubstituted amino acids into the peptide increased its helical content with respect to the unmodified control. In the i,i+4 peptide series, crosslinking neither stabilized nor destabilized the helix with respect to the corresponding uncrosslinked modified peptide; the reasons for this effect are not apparent from inspection of models. RCM crosslinking of the modified i,i+7 peptides produced effects ranging from 21% destabilization to significant stabilization of α-helical structure. Specifically, the helical content of the $R_{i,i+7}S(9)$ and (10) peptides decreased by 21% and 12% following RCM, whereas that of the $R_{i,i+7}S(11)$ peptide increased by 26%. Crosslinking of the $R_{i,i+7}S(12)$ peptide produced cis and trans double bond isomers one of which was more stabilizing than the other (18% vs 7%)[14]. The overall trends seen in the $R_{i,i+7}S$ series can be rationalized as follows: crosslinks of 9 and 10 carbons are too short to permit the formation of an unstrained helix, 11 carbons provides the optimal fit, and 12 carbons are longer than necessary and therefore do not constrain the helix as effectively as the 11 carbon crosslink. Importantly, the introduction and crosslinking of two modified amino acids as an 11 atom hydrocarbon chain stabilizes the helix by 44% when compared to an unmodified control peptide, an extent that is comparable to the best seen with other crosslinking systems[6]. As determined by sedimentation equilibrium, all of the peptides were monomeric under the conditions of the circular dichroism experiments, indicating that the helix induction is not due to aggregation[15].

To assess the effect of the olefin in the crosslink on helix-stability, we reduced the double bonds in the $R_{i,i+7}S$ series by transfer hydrogenation on the solid phase[16,17], purified the saturated, crosslinked peptides and determined their helical content by CD. Remarkably, the helical properties of the entire hydrogenated $R_{i,i+7}S(9-12)$ peptide series was indistinguishable from that of the corresponding olefin containing peptides.

Cleavage by proteases is one of the main pathways for inactivation of peptides in a biological setting. As all known proteases bind their substrates in an extended rather than helical conformation, inducing helical structure is expected to confer protease stability, leading to increased potency in vivo. As an in vitro test of this concept, we took advantage of the fact that the crosslinked stretch of our peptides contains a lysine residue, which can be targeted by the protease trypsin. As expected, the unmodified control peptide is highly susceptible to cleavage by trypsin ($k=2.38$ $M^{-1}$ $s^{-1}$) (Table 2). Incorporation of the two unnatural amino acids at the i and i+7 positions, without crosslinking, decreases the cleavage rate by almost 5 fold, consistent with the helix-stabilizing effects noted above. Metathesis and subsequent hydrogenation produced a further stabilization, the magnitude of which is markedly dependent on the length of the crosslink. The extent of this crosslink-dependent stabilization precisely mirrored the extent of helix induction, being most pronounced for the $R_{i,i+7}S(11)$ peptide. Overall, the incorporation of the crosslink unit stabilizes this peptide toward trypsin digestion by 41 fold.

The major goal of this research program is to improve the pharmacological properties of α-helical peptides through synthetic modification. The present report is an important first step toward that end. Here we show that an all-hydrocarbon crosslinking system can greatly increase the helical propensity and metabolic stability of peptides.

EXPERIMENTAL PROCEDURES

General: $^1$H (400 MHz) and $^{13}$C (100 MHz) NMR spectra were measured in DMSO-$d_6$ using tetramethylsilane as the standard for $^1$H NMR and the solvent resonance (39.5 ppm) for $^{13}$C NMR. Mass spectral data were obtained at the Harvard Mass Spectrometry Facility.

Synthesis of Boc protected α-methyl, α-alkenyl amino acids: The synthesis is as described by Williams' for Boc protected α-methyl, α-allyl amino acid with the following modifications. The second alkylation with allyl-iodide as the electrophile was performed at −78° C. The second alkylation, with 4-iodo-1-butene, 5-iodo-1-pentene, 6-iodo-1-hexene, or 8-iodo-1-hexene as the electrophile was performed at −40° C. (MeCN/N$_2$ (liquid)) with 3 equivalents of the electrophile and the reaction was stirred for 30 min after the dropwise addition of potassium bis(trimethylsilyl)amide. The second alkylation, when it involved the electrophile 4-iodo-1-butene resulted in lower yields (45%) presumably due to competing elimination of the 4-iodo-1-butene to 1,3-butadiene. Deblocking of the α,α disubstituted amino acids was performed using the sodium in liquid ammonia hydrogenolysis described as described by Williams[1].

Deprotection of the Boc protected α-methyl, α-alkenyl amino acids and acetylation with 9-fluorenylmethyl carbamate: The Boc protected α-methyl, α-alkenyl amino acid was dissolved in CH$_2$Cl$_2$ (to yield a concentration of 500 mM) and cooled to 0° C. To this solution, an equal volume of trifluoroacetic acid was added and the solution is allowed to stir for 30 min. The product was concentrated on a rotovap fitted with a dry ice/acetone cold finger to trap TFA. The residue is dried on high vacuum until it contained less than 2 equivalents of residual TFA by weight. To this residue was added a 50% water/acetone solution to 300 mM final concentration of amino acid, 3 equivalents of Na$_2$CO$_3$ and 1.05 equivalents of Fmoc-N-hydroxy-succinimide. The nonhomogenous mixture was stirred for 12 hours at room temperature. The mixture was then acidified to pH 3 using hydrochloric acid and extracted three times with ethyl acetate. The combined ethyl acetate extracts were then dried over anhydrous sodium sulfate, concentrated, and purified using flash chromatography using MeOH:CH$_2$Cl$_2$:AcOH (3:96:1).

(S)-N-(9-Fluorenylmethyl carbamate)-2-(2'-propenyl)alanine ("Fmoc-S-1$_1$"). $^1$H-NMR (400 MHz, DMSO-$d_6$) δ 7.90 (d, J=7.6 Hz, 2H), 7.73 (d, J=7.2 Hz, 2H), 7.42 (t, J=7.2 Hz, 2H), 7.34 (t, J=7.2 Hz, 2H), 5.70 (m, 1H), 5.07 (m, 2H), 4.25 (m, 3H), 2.65 (dd, J=13.6 Hz, J=7.2 Hz, 1H), 2.41 (dd, J=13.6 Hz, J=7.6 Hz, 1H), 1.30 (s, 3H); $^{13}$C-NMR (100 MHz, DMSO-$d_6$) δ 174.7, 154.5, 143.6, 140.5, 133.0, 127.4, 126.9, 125.1, 119.9, 118.4, 65.2, 57.8, 46.7, 22.4, 21.1; HRMS calcd for C$_{21}$H$_{21}$NO$_4$ (M+Na) 352.1549, found 352.1561.

(S)-N-(9-Fluorenylmethyl carbamate)-2-(2'-butenyl)alanine ("Fmoc-S-1$_2$"). $^1$H-NMR (400 MHz, DMSO-$d_6$) δ 7.90 (d, J=7.2 Hz, 2H), 7.73 (d, J=7.6 Hz, 2H), 7.42 (t, J=7.2 Hz, 2H), 7.33 (t, J=7.6 Hz, 2H), 5.79 (m, 1H), 5.01 (d, J=17.2 Hz, 1H), 4.95 (d, J=10.4 Hz, 1H), 4.25 (m, 3H), 1.93 (m, 3H), 1.75 (m, 1H), 1.35 (s, 3H); $^{13}$C-NMR (100 MHz, DMSO-$d_6$) δ 175.1, 154.6, 143.7, 140.6, 138.1, 127.5, 127.0, 125.2, 120.0, 118.4, 65.2, 58.1, 46.7, 35.6, 27.7, 22.4; HRMS calcd for C$_{22}$H$_{23}$NO$_4$ (M+H) 366.1705, found 366.1709.

(S)-N-(9-Fluorenylmethyl carbamate)-2-(2'pentenyl)alanine ("Fmoc-S-1$_3$"). $^1$H-NMR (400 MHz, DMSO-$d_6$) δ 7.894 (d, J=7.6 Hz, 2H), 7.723 (d, J=7.2 Hz, 2H), 7.418 (t, J=8 Hz, 2H), 7.330 (td, J=7.2 Hz, J=1.2 Hz, 2H), 5.775 (m, 1H), 5.001 (dd, J=17.2 Hz, J=1.2 Hz, 1H), 4.955 (dd, J=10.4 Hz, J=1.2 Hz, 1H), 4.229 (m, 3H), 1.994 (t, J=6.4 Hz, 2H), 1.764 (m, 1H), 1.665 (m, 1H), 1.326 (br, 5H); $^{13}$C-NMR (100 MHz, DMSO-$d_6$) δ 175.1, 154.5, 143.6, 140.5, 138.3, 127.4, 126.9, 125.1, 119.9, 114.8, 65.2, 58.2, 46.7, 36.3, 33.3, 22.6, 22.4; HRMS calcd for C$_{23}$H$_{25}$NO$_4$ (M+Na) 402.1682, found 402.1678.

(S)-N-(9-Fluorenylmethyl carbamate)-2-(2'-hexenyl)alanine ("Fmoc-S-1$_4$"). $^1$H-NMR (400 MHz, DMSO-$d_6$) δ 7.87 (d, J=7.6 Hz, 2H), 7.70 (d, J=7.2 Hz, 2H), 7.40 (t, J=7.2 Hz, 2H), 7.31 (t, J=7.2 Hz, 2H), 5.75 (m, 1H), 4.97 (dd, J=17.2 Hz, J=2 Hz, 1H), 4.91 (dt, J=10 Hz, J=1.2 Hz, 1H), 4.22 (m, 3H), 1.98 (m, 2H), 1.75 (m, 1H), 1.66 (m, 1H), 1.31 (m, 4H), 1.20 (s, 3H); $^{13}$C-NMR (100 MHz, DMSO-$d_6$) δ 175.5, 154.5, 143.6, 140.5, 138.4, 127.4, 126.9, 125.1, 119.9, 114.7, 65.2, 58.2, 46.7, 36.5, 33.2, 28.5, 22.8, 22.4; HRMS calcd for C$_{24}$H$_{27}$NO$_4$ (M+Na) 416.1838, found 416.1848.

(S)-N-(9-Fluorenylmethyl carbamate)-2-(2'-octenyl)alanine ("Fmoc-S-1$_6$"). $^1$H-NMR (400 MHz, DMSO-$d_6$) δ 7.89 (d, J=8 Hz, 2H), 7.72 (d, J=7.2 Hz, 2H), 7.42 (t, J=7.2 Hz, 2H), 7.33 (td, J=7.2 Hz, J=0.8 Hz, 2H), 5.78 (m, 1H), 4.98 (d, J=17 Hz, 1H), 4.93 (d, J=10 Hz, 1H), 4.23 (m, 3H), 1.99 (dt, J=7.2 Hz, J=6.8 Hz, 2H), 1.76 (m, 1H), 1.68 (m, 1H), 1.33 (br, 4H), 1.23 (br, 7H); $^{13}$C-NMR (100 MHz, DMSO-$d_6$) δ 175.0, 154.5, 143.6, 140.5, 138.5, 127.4, 126.8, 125.1, 119.9, 114.4, 65.2, 58.2, 46.7, 36.6, 33.2, 29.0, 28.4, 28.2, 23.1, 22.4; HRMS calcd for C$_{26}$H$_{31}$NO$_4$ (M+Na) 444.2151, found 444.2151.

(R)-N-(9-Fluorenylmethyl carbamate)-2-(2'-propenyl)alanine ("Fmoc-R-1$_1$"). $^1$H-NMR (400 MHz, DMSO-$d_6$) δ 7.90 (d, J=7.6 Hz, 2H), 7.73 (d, J=7.2 Hz, 2H), 7.42 (t, J=7.2 Hz, 2H), 7.34 (t, J=6.4 Hz, 2H), 5.69 (m, 1H), 5.06 (m, 2H), 4.25 (m, 3H), 2.65 (dd, J=13.6 Hz, J=6.8 Hz, 1H), 2.42 (dd, J=13.2 Hz, J=7.6 Hz, 1H) 1.30 (s, 3H); $^{13}$C-NMR (100 MHz, DMSO-$d_6$) δ 174.7, 154.5, 143.6, 140.5, 133.0, 127.4, 126.9, 125.1, 119.9, 118.4, 65.2, 57.8, 46.7, 22.4, 21.1; HRMS calcd for C$_{21}$H$_{21}$NO$_4$ (M+Na) 374.1369, found 374.1373.

(R)-N-(9-Fluorenylmethyl carbamate)-2-(2'-pentenyl)alanine ("Fmoc-R-1$_3$"). $^1$H-NMR (400 MHz, DMSO-$d_6$) δ 7.90 (d, J=7.6 Hz, 2H), 7.73 (d, J=7.6 Hz, 2H), 7.42 (t, J=7.6 Hz, 2H), 7.33 (t, J=7.6 Hz, 2H), 5.78 (m, 1H), 5.00 (d, J=17.6 Hz, 1H), 4.96 (d, J=10.4 Hz, 1H), 4.24 (m, 3H), 1.99 (m, 2H), 1.78 (m, 1H), 1.68 (m, 1H), 1.33 (br, 5H); $^{13}$C-NMR (100 MHz, DMSO-$d_6$) δ 175.1, 154.5, 143.6, 140.5, 138.3, 127.4, 126.9, 125.1, 119.9, 114.8, 65.2, 58.2, 46.7, 36.2, 33.3, 22.6, 22.4; HRMS calcd for $C_{23}H_{25}NO_4$ (M+H) 380.1862, found 380.1881.

(R)-N-(9-Fluorenylmethyl carbamate)-2-(2'-hexenyl)alanine ("Fmoc-R-$1_1$"). $^1$H-NMR (400 MHz, DMSO-$d_6$) δ 7.90 (d, J=7.2 Hz, 2H), 7.73 (d, J=7.2 Hz, 2H), 7.42 (t, J=7.6 Hz, 2H), 7.33 (t, J=7.2 Hz, 2H), 5.76 (m, 1H), 5.00 (dd, J=17.2 Hz, J=2 Hz, 1H), 4.94 (dt, J=10.4 Hz, J=0.8 Hz, 1H), 4.24 (m, 3H), 2.02 (br, 2H), 1.77 (m, 1H), 1.68 (m, 1H), 1.32 (br, 4H), 1.23 (br, 3H); $^{13}$C-NMR (100 MHz, DMSO-$d_6$) δ 175.1, 154.5, 143.6, 140.5, 138.4, 127.4, 126.9, 125.1, 119.9, 114.6, 65.2, 58.2, 46.7, 36.5, 33.2, 28.5, 22.7, 22.4; HRMS calcd for $C_{24}H_{27}NO_4$ (M+Na) 416.1838, found 416.1823.

Peptide Synthesis: The peptides were synthesized manually, using solid phase peptide and Fmoc chemistry on Rink Amide AM resin with a loading of 0.65 mmol/g resin. α,α-Di-substituted amino acids were coupled using O-(7-azabenzotriazol-1-yl)-1,1,3,3-tetramethyluronium hexafluorophosphate (HATU) as the activating agent, three equivalents of the amino acid, and coupling times were typically two hours. The following amino acid coupled to the free amine of the α,α-di-substituted amino acids was double coupled using HATU. The peptides were cleaved using standard protocols, purified using C18 reverse phase chromatography and their identities were confirmed using electrospray mass spectroscopy. The wild type peptide has the sequence: Ac-EWAETAAAK-FLAAHA-NH$_2$ (SEQ ID NO:1). The peptides synthesized in the $R_{i,i+7}S(x)$ series have the general sequence: Ac-EWAEyAAAKFLzAHA-NH$_2$ (SEQ ID NO:2) where (y,z) were substituted with the unnatural amino acid pairs (R-$1_3$,S-$1_3$), (R-$1_3$,S-$1_4$), (R-$1_4$,S-$1_4$), (R-$1_3$,S-$1_6$), and (R-$1_4$,S-$1_6$) for the peptides $R_{i,i+7}S(8)$, $R_{i,i+7}S(9)$, $R_{i,i+7}S(10)$, $R_{i,i+7}S(11)$, and $R_{i,i+7}S(12)$ respectively. The peptides synthesized in the $S_{i,i+4}S(x)$, $R_{i,i+4}R(x)$, and $R_{i,i+4}S(x)$ series have the general sequence: Ac-EWAETAAyKFLzAHA-NH$_2$ (SEQ ID NO:3) where (y,z) were substituted with the unnatural amino acid pairs (S-$1_1$,S-$1_3$), (S-$1_1$,S-$1_4$), (S-$1_3$,S-$1_3$), (R-$1_1$,R-$1_3$), (R-$1_1$,R-$1_4$), (R-$1_3$,R-$1_3$), (R-$1_1$,S-$1_2$), (R-$1_1$,S-$1_3$), and (R-$1_1$,S-$1_4$) for the peptides $S_{i,i+4}S(6)$, $S_{i,i+4}S(7)$, $S_{i,i+4}S(8)$, $R_{i,i+4}R(6)$, $R_{i,i+4}R(7)$, $R_{i,i+4}R(8)$, $R_{i,i+4}S(5)$, $R_{i,i+4}S(6)$, and $R_{i,i+4}S(7)$ respectively. Ac and NH$_2$ represent N-terminal acetylation and a C-terminal primary amide respectively.

Peptide metathesis and purification: 200 μL of 10 mM Bis(tricyclohexylphosphine)benzylidine ruthenium (IV) dichloride (Grubbs catalyst) in 1,2-dichloroethane was degassed and added to 20 mg of N-terminal capped peptide still bound to the solid support in a disposable fritted reaction vessel. The reaction was allowed to proceed at room temperature for two hours and then the catalyst was filtered off. The catalyst addition and 2 hour metathesis reaction was repeated once to drive the slow metathesis reactions to completion. The resin bound peptide was then washed, dried and cleaved according to standard Fmoc peptide cleavage protocols (95% TFA, 2.5% H$_2$O, 2.5% triisopropylsilane)[19]. The cleaved peptides are purified using C$_{18}$ reverse phase HPLC. All of the metathesized peptides elute before the unmetathesized starting material.

Olefin hydrogenation on solid support: Hydrogenation of olefin containing peptides on solid support was performed by adding 200 μL of a solution of 0.7 M 2,4,6 tri-isopropyl benzenesulfonyl hydrazide and 1.4 M piperidine in 1-methyl-2-pyrrolidinone to 20 mg of olefin containing peptide on solid support in a disposable fritted reaction vessel. The vessel was sealed and placed in a 47° C. water bath for two hours. After two hours the solution was filtered off and the hydrazine addition and reaction at 47° C. is repeated four more times. The progress of the reaction can be monitored by injecting the cleavage product of a few beads into an electrospray reverse phase LC mass spectrometer or by reverse phase HPLC monitored at 280 nm. The retention time of the hydrogenated peptides falls between the metathesized, unhydrogenated peptides and the unmetathesized peptides.

Circular dichroism: Circular dichroism spectra were collected on a Jasco J-710 spectropolarimeter at 4° C. A typical sample was prepared by lyophilizing a measured volume of peptide solution and then resuspending it in 3 ml of 0.1% TFA in water to obtain a solution with a 280 nm absorbance of approximately 0.06 absorbance units. The sample was placed in a 1 cm CD cuvette and the ultraviolet absorbance was measured. The circular dichroism spectrum was measured and a baseline CD spectrum of 0.1% TFA in water was subtracted from it. The baseline subtracted CD spectrum was then normalized using the 280 nm absorbance.

Analytical centrifugation: Sedimentation equilibrium experiments were performed on a Beckman Optima XL-A analytical centrifuge. The samples were centrifuged at 35,000 RPM at 4° C. and monitored at 280 nm. The data was fit to a single species model. The sedimentation equilibrium experiments were run on the identical samples from which circular dichroism spectra were recorded. All of the peptides fit to an ideal monomer indicating that the helix induction seen is not due to aggregation.

Peptide trypsin digest: A typical peptide trypsin digest experiment was performed by adding 5 μL of a 20×trypsin solution in 1 mM HCl to a 100 μL solution of peptide at 9 μM in 10% EtOH in 50 mM Tris at pH 8.3. The reaction was allowed to proceed at room temperature for 30 min at which time it was quenched by adding 100 μL of a 1% trifluoroacetic acid solution and frozen on dry ice. The sample was then thawed and injected into a reverse phase HPLC on a C18 column for quantitation at 280 nm. The cleavage rate constants were obtained by performing the digest experiments at multiple trypsin concentrations and fitting to a kinetic model that is first order in both enzyme and substrate concentration. Table 1

Percent conversions for a two hour metathesis reaction performed on solid support with 10 mM Grubbs catalyst in 1,2-dichloroethane. Percent conversion product/(product+ starting material) as determined by reverse phase HPLC.

TABLE 1

| Crosslink | % Conversion | Crosslink | % Conversion | Crosslink | % Conversion |
|---|---|---|---|---|---|
| $R_{i,i+7}S(8)$ | 0 | $S_{i,i+4}S(6)$ | 0 | $S_{i,i+4}R(6)$ | 0 |
| $R_{i,i+7}S(9)$ | 51 | $S_{i,i+4}S(7)$ | 68 | $S_{i,i+4}R(7)$ | 17 |
| $R_{i,i+7}S(10)$ | 77 | $S_{i,i+4}S(8)$ | >98 | $S_{i,i+4}R(8)$ | >98 |
| $R_{i,i+7}S(11)$ | >98 | | | | |
| $R_{i,i+7}S(12)$ | >98 | | | | |

TABLE 2

| | Cleavage rate constant ($M^{-1} s^{-1}$) | |
|---|---|---|
| Crosslink | Unmetathesized | Metathesized and hydrogenated |
| Control | 2.39 | |
| $R_{i,i+7}S(9)$ | | 0.37 |
| $R_{i,i+7}S(10)$ | | 0.34 |
| $R_{i,i+7}S(11)$ | 0.50 | 0.058 |
| $R_{i,i+7}S(12)$ | | 0.12 |

REFERENCES AND NOTES

1) Gante, J. *Angew. Chem. Int. Ed. Engl.* 1994, 33, 1699-1720.
2) Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. *Science* 1997, 275, 983-6.
3) Kussie, P. H.; Gorina, S.; Marechal, V.; Elenbaas, B.; Moreau, J.; Levine, A. J.; Pavletich, N. P. *Science* 1996, 274, 948-53.
4) Andrews, M. J. I.; Tabor, A. B. *Tetrahedron* 1999, 55, 11711-11743.
5) Jackson, D. Y.; King, D. S.; Chmielewski, J.; Singh, S.; Schultz, P. G. *J. Am. Chem. Soc.* 1991, 113, 9391-9392.
6) Phelan, J. C.; Skelton, N. J.; Braisted, A. C.; McDowell, R. S. *J. Am. Chem. Soc.* 1997, 119, 455-460.
7) Bracken, C.; Gulyas, J.; Taylor, J. W.; Baum, J. *J. Am. Chem. Soc.* 1994, 116, 6431-6432.
8) Blackwell, H. E.; Grubbs, R. H. *Angew. Chem. Int. Edn. Engl.* 1998, 37, 3281-3284.
9) Bierzynski, A.; Kim, P. S.; Baldwin, R. L. *Proc. Natl. Acad. Sci USA* 1982, 79, 2470-2474.
10) The wild type peptide has the sequence: Ac-EWA-ETAAAKFLAAHA-NH$_2$ (SEQ ID NO:1). The peptides synthesized in the R$_{i,i+7}$S(x) series have the general sequence: Ac-EWAEyAAAKFLzAHA-NH$_2$ (SEQ ID NO:2) where (y,z) were substituted with the unnatural amino acid pairs (R-1$_3$,S-1$_3$), (R-1$_3$,S-1$_4$), (R-1$_4$,S-1$_4$), (R-1$_3$,S-1$_6$), and (R-1$_4$,S-1$_6$) for the peptides R$_{i,i+7}$S(8), R$_{i,i+7}$S(9), R$_{i,i+7}$S(10), R$_{i,i+7}$S(11), and R$_{i,i+7}$S(12) respectively. The peptides synthesized in the S$_{i,i+4}$S(x), R$_{i,i+4}$R(x), and R$_{i,i+4}$S(x) series have the general sequence: Ac-EWAETAAyKFLzAHA-NH$_2$ (SEQ ID NO:3) where (y,z) were substituted with the unnatural amino acid pairs (S-1$_1$, S-1$_3$), (S-1$_1$,S-1$_4$), (S-1$_3$,S-1$_3$), (R-1$_1$,R-1$_3$), (R-1$_1$,R-1$_4$), (R-1$_3$,R-1$_3$), (R-1$_1$,S-1$_2$), (R-1$_1$,S-1$_3$), and (R-1$_1$,S-1$_4$) for the peptides S$_{i,i+4}$S(6), S$_{i,i+4}$S(7), S$_{i,i+4}$S(8), R$_{i,i+4}$R(6), R$_{i,i+4}$R(7), R$_{i,i+4}$R(8), R$_{i,i+4}$S(5), R$_{i,i+4}$S(6), and R$_{i,i+4}$S(7) respectively. Ac and NH$_2$ represent N-terminal acetylation and a C-terminal primary amide respectively.
11) Clark, T. D.; Ghadiri, M. R. *J. Am. Chem. Soc.* 1995, 117, 12364-12365.
12) Greenfield, N.; Fasman, G. D. *Biochemistry* 1969, 8, 4108-4116.
13) Kaul, R.; Balaram, P. *Bioorganic and Medicinal Chemistry* 1999, 7, 105-117.
14) C18 reverse phase HPLC of R$_{i,i+7}$S(12) shows two separable product peaks (a) and (b) that have identical molecular masses (1760 Daltons). Peak (a) has an NMR peak at ($\delta$=5.49) and peak (b) has an NMR peak at ($\delta$=5.52). Hydrogenated R$_{i,i+7}$S(12) is a single peak by reverse phase C18 HPLC.
15) See "Analytical Centrifugation" in supporting information.
16) Lacombe, P.; Castagner, B.; Gareau, Y.; Ruel, R. *Tetrahedron Letters* 1998, 39, 6785-6786.
17) Cusack, N. J.; Reese, C. B.; Risius, A. C.; Roozpeikar, B. *Tetrahedron* 1976, 32, 2157-2162.
18) Williams, R. M.; Im, M. *J. Am. Chem. Soc.* 1991, 113, 9276-9286.
19) Novabiochem *Novabiochem Catalog & Peptide Synthesis Handbook*, 1997.

EQUIVALENTS

Those skilled in the art will recognize, or be able to ascertain using no more than routine experimentation, numerous equivalents to the inventive stabilized compounds and methods of use thereof described herein. Such equivalents are considered to be within the scope of this invention and are covered by the following claims.

---

We claim:

1. A method for synthesizing a stabilized helical peptide comprising:
   a) synthesizing a peptide from a selected number of amino acids, wherein the peptide comprises at least two alpha, alpha-disubstituted amino acids, further wherein each alpha, alpha-disubstituted amino acid comprises a moiety capable of undergoing reaction to form a carbon-carbon bond;
   wherein each of the alpha, alpha-disubstituted amino acids comprises at the alpha position a methyl group; and
   b) contacting the peptide with a reagent to generate at least one cross-linker connecting at least two moieties to result in a stabilized helical peptide,
   wherein the at least two alpha, alpha disubstituted amino acids are cross-linked.

2. A method for synthesizing a stabilized peptide comprising:
   a) synthesizing a peptide from a selected number of amino acids, wherein the peptide comprises at least two alpha, alpha-disubstituted amino acids, further wherein each alpha, alpha-disubstituted amino acid comprises a moiety capable of undergoing reaction to form a carbon-carbon bond;
   wherein each of the alpha, alpha-disubstituted amino acids is an alpha-methyl, alpha-alkenyl amino acid; and
   b) contacting the peptide with a reagent to generate at least one cross-linker connecting at least two moieties to result in a stabilized peptide.

3. The method of claim 2, wherein the alpha-methyl, alpha-alkenyl amino acid comprises a pentenyl or octenyl side chain.

4. The method of claim 1, wherein the length of the cross-linked moieties between the two alpha positions is 7 or 8 carbon atoms.

5. The method of claim 1, wherein the length of the cross-linked moieties between the two alpha positions is 9 to 12 carbon atoms.

6. The method of claim 1 or 2, wherein the reaction is olefin metathesis.

7. The method of claim 1 or 2, wherein the reagent is a metathesis catalyst.

8. The method of claim 1 or 2, wherein the reagent is a Group VIII transition metal carbene catalyst.

9. The method of claim 1 or 2, wherein the reagent is a Group VIII transition metal carbene catalyst that is a ruthenium metathesis catalyst.

10. The method of claim 1 or 2, wherein the peptide has exactly two alpha, alpha-disubstituted amino acids.

11. The method of claim 1 or 2, wherein two of the at least two alpha, alpha-disubstituted amino acids have an S configuration.

12. The method of claim 1 or 2, wherein one of the at least two alpha, alpha-disubstituted amino acid has an S configuration and one of the at least two alpha, alpha-disubstituted amino acid has an R configuration.

13. The method of claim 1 or 2, wherein the peptide comprises three alpha, alpha-disubstituted amino acids.

14. The method of claim 1 or 2, wherein the cross-linkers is an alkene cross-linker.

15. The method of claim 1 or 2, wherein the cross-linker is an alkene cross-linker; and further comprising reducing the alkene cross-linker, to result in an alkane cross-linker.

16. The method of claim 2, wherein the stabilized peptide is helical.

17. The method of claim 2, wherein the length of the cross-linked moieties between the two alpha positions is 7 or 8 carbon atoms.

18. The method of claim 2, wherein the length of the cross-linked moieties between the two alpha positions is 9 to 12 carbon atoms.

* * * * *

SEQUENCE LISTING

```
<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Glu Trp Ala Glu Thr Ala Ala Ala Lys Phe Leu Ala Ala His Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Unnatural amino acid
<220> FEATURE:
<221> NAME/KEY: MISC_FEATURE
<222> LOCATION: (12)..(12)
<223> OTHER INFORMATION: Unnatural amino acid

<400> SEQUENCE: 2

Glu Trp Ala Glu Xaa Ala Ala Ala Lys Phe Leu Xaa Ala His Ala
```

```
1               5                   10                  15
```

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Unnatural amino acid
<220> FEATURE:
<221> NAME/KEY: MISC_FEATURE
<222> LOCATION: (12)..(12)
<223> OTHER INFORMATION: Unnatural amino acid

<400> SEQUENCE: 3

```
Glu Trp Ala Glu Thr Ala Ala Xaa Lys Phe Leu Xaa Ala His Ala
1               5                   10                  15
```

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Unnatural amino acid
<220> FEATURE:
<221> NAME/KEY: MISC_FEATURE
<222> LOCATION: (8)..(8)
<223> OTHER INFORMATION: Unnatural amino acid
<220> FEATURE:
<221> NAME/KEY: MISC_FEATURE
<222> LOCATION: (15)..(15)
<223> OTHER INFORMATION: Unnatural amino acid

<400> SEQUENCE: 4

```
Xaa Trp Ala Glu Thr Ala Ala Xaa Lys Phe Leu Ala Ala His Xaa
1               5                   10                  15
```

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

```
Gly Gln Val Gly Arg Gln Leu Ala Ile Ile Gly Asp Asp Ile Asn Arg
1               5                   10                  15
```

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Unnatural amino acid
<220> FEATURE:
<221> NAME/KEY: MISC_FEATURE
<222> LOCATION: (9)..(9)
<223> OTHER INFORMATION: Unnatural amino acid

<400> SEQUENCE: 6

Gly Gln Val Gly Xaa Gln Leu Ala Xaa Ile Gly Asp Asp Ile Asn Arg
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Unnatural amino acid
<220> FEATURE:
<221> NAME/KEY: MISC_FEATURE
<222> LOCATION: (13)..(13)
<223> OTHER INFORMATION: Unnatural amino acid

<400> SEQUENCE: 7

Gly Gln Val Gly Arg Gln Leu Ala Xaa Ile Gly Asp Xaa Ile Asn Arg
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Unnatural amino acid
<220> FEATURE:
<221> NAME/KEY: MISC_FEATURE
<222> LOCATION: (13)..(13)
<223> OTHER INFORMATION: Unnatural amino acid

<400> SEQUENCE: 8

Gly Gln Val Gly Arg Xaa Leu Ala Ile Ile Gly Asp Xaa Ile Asn Arg
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Unnatural amino acid
<220> FEATURE:
<221> NAME/KEY: MISC_FEATURE
<222> LOCATION: (12)..(12)
<223> OTHER INFORMATION: Unnatural amino acid

<400> SEQUENCE: 9

Gly Gln Val Gly Xaa Gln Leu Ala Ile Ile Gly Xaa Asp Ile Asn Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Leu Ser Gln Glu Thr Phe Ser Asp Leu Trp Lys Leu Leu Pro Glu Asn
1               5                   10                  15

```
<210> SEQ ID NO 11
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Unnatural amino acid
<220> FEATURE:
<221> NAME/KEY: MISC_FEATURE
<222> LOCATION: (12)..(12)
<223> OTHER INFORMATION: Unnatural amino acid

<400> SEQUENCE: 11

Leu Ser Gln Glu Xaa Phe Ser Asp Leu Trp Lys Xaa Leu Pro Glu Asn
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Unnatural amino acid
<220> FEATURE:
<221> NAME/KEY: MISC_FEATURE
<222> LOCATION: (11)..(11)
<223> OTHER INFORMATION: Unnatural amino acid

<400> SEQUENCE: 12

Leu Ser Gln Xaa Thr Phe Ser Asp Leu Trp Xaa Leu Leu Pro Glu Asn
1               5                   10                  15
```